US006673580B2

(12) United States Patent
Koren et al.

(10) Patent No.: US 6,673,580 B2
(45) Date of Patent: Jan. 6, 2004

(54) IDENTIFICATION AND MODIFICATION OF IMMUNODOMINANT EPITOPES IN POLYPEPTIDES

(75) Inventors: Eugen Koren, San Francisco, CA (US); John Hok Nin Lowe, Pleasanton, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/872,702

(22) Filed: Jun. 1, 2001

(65) Prior Publication Data

US 2003/0077756 A1 Apr. 24, 2003

Related U.S. Application Data

(60) Provisional application No. 60/243,913, filed on Oct. 27, 2000.

(51) Int. Cl.[7] .................................................. C12N 15/64
(52) U.S. Cl. ................ 435/91.4; 435/91.41; 435/91.42; 435/69.1; 435/440; 435/7.1; 435/325; 536/23.5; 530/403; 514/2
(58) Field of Search ................................. 530/350, 351, 530/399, 403; 435/7.1, 69.1–69.7, 91.1, 91.4–91.42, 440, 325; 536/23.5, 23.1; 514/2

(56) References Cited

U.S. PATENT DOCUMENTS

| 3,903,068 A | 9/1975 | Ruttenberg |
| 4,179,337 A | 12/1979 | Davis et al. |
| 4,301,144 A | 11/1981 | Iwashita et al. |
| 4,399,216 A | 8/1983 | Axel et al. |
| 4,496,689 A | 1/1985 | Mitra |
| 4,640,835 A | 2/1987 | Shimizu et al. |
| 4,657,760 A | 4/1987 | Kung et al. |
| 4,670,417 A | 6/1987 | Iwasaki et al. |
| 4,791,192 A | 12/1988 | Nakagawa et al. |
| 4,943,529 A | 7/1990 | Van den Berg et al. |
| 4,946,783 A | 8/1990 | Beckwith et al. |
| 5,010,182 A | 4/1991 | Brake et al. |
| 5,128,529 A | 7/1992 | Nagaoka et al. |
| 5,206,344 A | 4/1993 | Katre et al. |
| 5,225,212 A | 7/1993 | Martin et al. |
| 5,364,934 A | 11/1994 | Drayna et al. |
| 5,585,250 A | 12/1996 | Garrity |
| 5,593,666 A | 1/1997 | McDonald |
| 5,654,010 A | 8/1997 | Johnson et al. |
| 5,766,898 A | 6/1998 | Loevborg |
| 5,795,569 A | 8/1998 | Bartley et al. |
| 5,821,047 A | 10/1998 | Garrard et al. |
| 5,853,724 A | 12/1998 | Garrity et al. |
| 5,872,215 A | 2/1999 | Osbourne et al. |
| 5,940,307 A | 8/1999 | Fischbarg et al. |
| 5,951,980 A | 9/1999 | Collen |
| 5,969,108 A | 10/1999 | McCafferty et al. |

FOREIGN PATENT DOCUMENTS

| DD | 266710 A | 4/1989 |
| EP | 0 036 776 | 9/1981 |
| EP | 0 073 657 | 3/1983 |
| EP | 0 117 058 | 8/1984 |
| EP | 0 117 060 | 8/1984 |
| EP | 0 139 383 | 5/1985 |
| EP | 0 183 070 | 6/1986 |
| EP | 0 244 234 | 11/1987 |
| EP | 0 251 446 A2 | 1/1988 |
| EP | 0 307 247 A3 | 3/1989 |

(List continued on next page.)

OTHER PUBLICATIONS

H.U. Lutz, "How pre–existing, germline–derived antibodies and complement mayhelp induce a primary immune response to nonself" Scand. J. Immunol. 49:224–228, 1999.*

V. I. Seledtsov et al., "A possible role or pre–existing IgM/IgG antibodies in determining immune response type" Immunology and Cell Biol. 75:176–180, 1997.*

Muto, T. et al., "Functional Analysis of the C–terminal Region of Recombinant Human Thrombopoietin", *The Journal of Biological Chemistry*, vol. 275, No. 16, pp. 12090–12094 (Apr. 21, 2000).

Arlian, L.G. et al., "Antigentic and Allergenic Characterization of the Enzymes Alcalase and Savinase by Crossed Immunoelectrophoresis and Cross Radioimmunoelectrophoresis", *Int. Arch. Allergy Appl. Immunol.*, 91:278–284 (1990).

Collen, D. et al., "Recombinant Staphylokinase Variants With Altered Immunoreactivity—I: Construction and Characterization", *Circulation*, vol. 94, No. 2, pp. 197–206 (Jul. 15, 1996).

Collen, D. et al., "Recombinant Staphylokinase Variants With Altered Immunoreactivity—II: Thrombolytic Properties and Antibody Induction", *Circulation*, vol. 94, No. 2, pp. 207–216 (Jul. 15, 1996).

Collen, D. et al., "Recombinant Staphylokinase Variants With Altered Immunoreactivity—III: Species Variability of Antibody Binding Patterns", *Circulation*, vol. 95, No. 2, pp. 455–462 (Jan. 21, 1997).

Collen, D. et al., "Recombinant Staphylokinase Variants With Altered Immunoreactivity—IV: Identification of Variants With Reduced Antibody Induction but Intact Potency", *Circulation*, vol. 95, No. 2, pp. 463–472 (Jan. 21, 1997).

(List continued on next page.)

*Primary Examiner*—Lorraine Spector
(74) *Attorney, Agent, or Firm*—Merchant & Gould P.C.

(57) ABSTRACT

The invention provides for methods of modifying immunodominant epitopes on polypeptides, preferably polypeptides intended for therapeutic use. Knowledge of immunodominant epitopes prior to clinical use of polypeptides would be useful to design and engineer less immunogenic molecules. The invention provides for methods of identifying immunodominant epitopes and modifying an immunodominant epitope to reduce the immune response to the polypeptide while still retaining a substantial therapeutic activity of the polypeptide. The modified polypeptides are useful therapeutically.

26 Claims, 8 Drawing Sheets

FOREIGN PATENT DOCUMENTS

Figure 1:
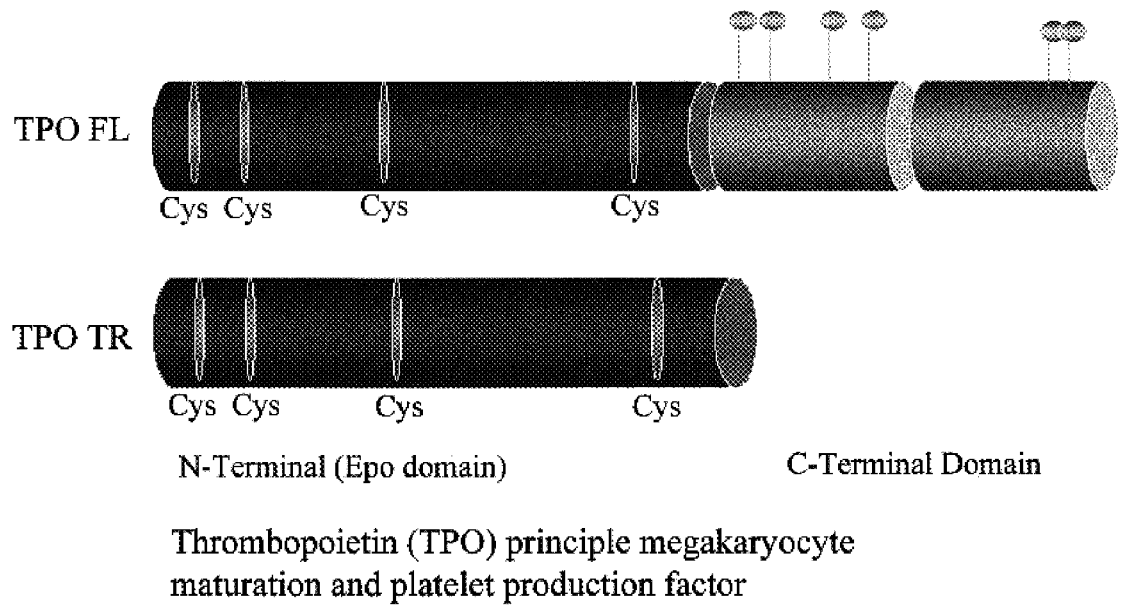

| | | |
|---|---|---|
| EP | 0 307 247 A2 | 3/1989 |
| EP | 0 362 179 A3 | 4/1990 |
| EP | 0 362 179 A2 | 4/1990 |
| EP | 0 394 538 A1 | 10/1990 |
| EP | 0 402 226 A1 | 12/1990 |
| EP | 0 721 982 A1 | 7/1996 |
| GB | 2 211 504 A | 7/1989 |
| WO | WO 87/05330 | 9/1987 |
| WO | WO 89/05859 | 6/1989 |
| WO | WO 89/06279 | 7/1989 |
| WO | WO 90/13646 | 11/1990 |
| WO | WO 91/00345 | 1/1991 |
| WO | WO 91/00357 | 1/1991 |
| WO | WO 92/10755 | 6/1992 |
| WO | WO 95/18858 | 7/1995 |
| WO | WO 96/07399 A1 | 3/1996 |
| WO | WO 96/21016 A3 | 7/1996 |
| WO | WO 96/21016 A2 | 7/1996 |
| WO | WO 96/40072 A3 | 12/1996 |
| WO | WO 96/40072 A2 | 12/1996 |
| WO | WO 97/03692 | 2/1997 |
| WO | WO 97/26907 | 7/1997 |
| WO | WO 98/52598 | 11/1998 |
| WO | WO 99/03887 | 1/1999 |
| WO | WO 99/38978 | 8/1999 |
| WO | WO 99/53038 | 10/1999 |
| WO | WO 00/34317 | 6/2000 |

OTHER PUBLICATIONS

Collen, D. et al., "Polyethylene Glycol–Derivatized Cysteine–Substitution Variants of Recombinant Staphylokinase for Single–Bolus Treatment of Acute Myocardial Infarction", *Circulation*, pp. 1766–1772 (Oct. 10, 2000).

Collins, S.P., "Absence of continuous epitopes in the house dust mite major allergens *Der p I* from *Dermatophagoides pteronyssinus* and *Der f I* from *Dermatophagoides farinae*", *Clinical and Experimental Allergy*, 26:36–42 (1996).

Creighton, T., "Proteins: Structures and Molecular Principles", p. 4 (1984).

Favre, C. et al., "Epitope Mapping of Recombinant Human Gamma Interferon Using Monoclonal Antibodies", *Molecular Immunology*, vol. 26, No. 1, pp. 17–25 (1989).

Geysen, H. et al., "Chemistry of Antibody Binding to a Protein", *Science*, 235:1184–1190 (Mar. 6, 1987).

Geysen, H. et al., "Cognitive Features of Continuous Antigenic Determinants", *Journal of Molecular Recognition*, vol. 1, No. 1, pp. 32–41 (1988).

Jemmerson, R. et al., "Fine manipulation of antibody affinity for synthetic epitopes by altering peptide structure: antibody binding to looped peptides", *Eur. J. Immunol.*, 20:579–585 (1990).

Laroche, Y. et al., "Recombinant staphylokinase variants with reduced antigenicity due to elimination of B–lymphocyte epitopes", *Blood*, vol. 96, No. 4, pp. 1425–1432 (Aug. 15, 2000).

Leyte, A. et al., "Inhibition of human coagulation Factor VIII by monoclonal antibodies", *Biochem. J.*, 263:187–194 (1989).

Rabijns, A. et al., "Three–dimensional structure of staphylokinase, a plasminogen activator with therapeutic potential", Correspondence, *Nature Structural Biology*, vol. 4, No. 5 (May 1997).

Quijada, L. et al., "Analysis of the antigenic properties of the L. infantum Hsp70: Design of synthetic peptides for specific serodiagnosis of human leishmaniasis", *Immunlogy Letters*, vol. 63(3), 169–174 (1998), Abstract only.

Lackner, K. et al., "Autoantibodies against human calpastatin in rheumatoid arthritis: epitope mapping and analysis of patient sera", *British Journal of Rheumatology*, 37(11):1164–1171 (Nov. 1998), Abstract only.

Hanes, J. et al., "In–vitro selection and evolution of funtional proteins by using ribosome display", *Proc. Natl. Acad. Sci USA*, 94(10):4937–4942 (May 13, 1997), Abstract only.

Angel, S. et al., "During canine leishmaniasis a protein belonging to the 83–kda heat–shock protein family elicits a strong humoral response", *Acta Tropica*, 62(1):45–46 (Sep. 1996), Abstract only.

Dutta, S. et al., "Molecular cloning and analysis of recombinant major antigens of *Ehrlichia risticii*" *Infection and Immunity*, 59(3):1162–1169 (Mar. 1991), Abstract only.

Scandella, D. et al., "Epitope mapping of human Factor VIII inhibitor antibodies by deletion analysis of factor VIII fragments expressed in *Escherichia coli*", *Proc. Natl. Acad. Sci USA*, 85:6152–6156 (Aug. 1988).

Schoofs, P. et al., "Epitopes of an influenza viral peptide recognized by antibody at single amino acid resolution", *The Journal of Immunology*, vol. 140, No. 2, pp. 611–616 (Jan. 15, 1988).

Stewart, T. et al., "Transgenic Mice as a Model to Test the Immunogenicity of Proteins Altered by Site–specific Mutagenesis", *Mol. Biol. Med.*, 6:275–281 (1989).

Storch, M. et al., "Specificity of Monoclonal Anti–Human Insulin Antibodies", *Diabetes*, 36:1005–1009 (Sep. 1987).

Walsh, B.J. et al., "A method for the detection of IgE binding sequences of allergens based on a modification of epitope mapping", *Journal of Immunological Methods*, 121:275–280 (1989).

Zachariae, H. et al., "Detergent Enzymes and Occupational Safety", *Allergy*, 36:513–516 (1981).

"Welcome to the ThromboGenics Ltd. homepage", http://www.thrombogenics.com/TestWelcome.html, 5 pages (Last Update: Fri., Jun. 29, 2001, Printed Nov. 20, 2001).

Ahmed, et al., *A new rapid and simple non–radioactive assay to monitor and determine the proliferation of lymphocytes: an alternative to Hthymidine incorporation assay*, Jour. of Immunological Methods 170:211–224 (1994).

Altschul et al., *Local Alignment Statistics*, Methods in Enzymology 266: 460–480 (1996).

Altschul et al., *Gapped BLAST and PSI–BLAST: a new generation of protein database search programs*, Nucleic Acids Research vol. 25, No. 17, pp. 3389–3402 (1997).

Andreason, *Electroporation as a technique for the transfer of macromolecules into mammalian cell lines*, Tissue Culture Methods vol. 15, No. 2, 56–62 (1993).

Aplin et al., *Preparation, Properties, and Applications of Carbohydrate Conjugates of Proteins and Lipids*, Critcial Reviews in Biochemistry, pp. 259–306 (May 1981).

Ballance et al., *Transformation of Aspergillus nidulans by the Orotidine–5'–Phosphate Decarboxylase Gene of Neurospora crassa*, Biochemical and Biophysical Research Communications vol. 112, No. 1, 284–289 (1983).

Beach et al. *High–frequency transformation of the fission yeast Schizosaccharomyces pombe*, Nature vol. 290, No. 5802, pp. 140–142 (1981).

C. Anthony, *Metabolism in the methylotrophic yeasts*, The Biochemistry of Methylotrophs pp. 269–295 (1982).

Carter et al., *Improved oligonucleotide site–directed mutagenesis using M13 vectors*, Nucleic Acids Research vol. 13, No. 12, pp. 4431–4443 (1985).

Case et al., *Efficient transformation of Neurospora crassa by utilizing hybrid plasmid DNA*, Proceedings of the National Academy of Sciences vol. 76, No. 10, pp. 5259–5263 (1979).

Chang et al., *Pheonotypic expression in E. coli of a DNA sequence encoding for mouse dihydrofolate reductase*, Nature vol. 275, No. 5681, pp. 617–624 (1978).

Chothia, *The Nature of the Accessible and Buried Surfaces in Proteins*, Journal of Molecular Biology vol. 105, No. 1, pp. 1–14 (1976).

Cleland, *Design and Production of Single–Immunization Vaccines Using Polylactide Polyglycolide Microsphere Systems, Vaccine Design:* The Submit and Adjuvant Approach, pp. 439–462 (1995).

Creighton, Proteins: *Structures and Modecular Principles*, W.H. Freeman & Co., San Francisco, pp. 79–86 (1983).

Cunningham et al., *High–Resolution Epitope Mapping of hGH–Receptor Interactions by Alanine–Scanning Mutagenesis*, Science vol. 244:1017–1116 (1989).

DeBoer et al., *The tac promoter: A functional hybrid derived from the trp and lac promoters*, Proceedings of the National Academy of Sciences vol. 80, No. 1, pp. 21–25 (1983).

Edge et al., *Deglycosylation of Glycoproteins by Trifluoromethanesulfonic Acid*, Analytical Biochemistry vol. 118, No. 1, pp. 131–137 (1981).

Fleer et al., *Stable Multicopy Vectors for High–Level Secretion of Recombinant Human Serum Albumin by Kluyveromyces Yeasts*, Biotechnology vol. 9, pp. 968–975 ((1991).

Gething et al., *Cell–surface expression of influenza haemagglutinin from a cloned DNA copy of the RNA gene*, Nature vol. 293, No, 5834, pp. 620–625 (1981).

Goeddel et al., *Direct expression in Escherichia coli of a DNA sequence coding for human growth hormone*, Nature, vol. 281, No. 5732, pp. 544–548 (1979).

Goeddel et al., *Synthesis of human fibroblast interferon by E. coli*, Nucleic Acids Research, vol. 8, No. 18, pp. 4057–4074 (1980).

Graham et al., *A New Technique for the Assay of Infectivity of Human Adenovirus 5 DNA*, Virology, vol. 52, No. 2, pp. 456–467 (1973).

Hess et al., *Cooperation of Glycolytic Enzymes*, Advances in Enzyme Regulation, vol. 7, pp. 149–167 (1968).

Hitzeman et al., *Isolation and Characterization of the Yeast 3–Phosphoglycerokinase Gene (PGK) by an Immunological Screening Technique,* The Journal of Biological Chemistry, vol. 255, No. 24, pp. 12073–12080 (1980).

Holland et al., *Isolation and Identification of Yeast Messenger Ribonucleic Acids Coding for Enolase, Glyceraldehye–3–phosphate Dehydrogenase, and Phosphoglycerate Kinase*, Biochemistry, vol. 17, No. 23, pp. 4900–4907 (1978).

Hora et al., *Controlled Released of Interleukin–2 from Biodegradable Microspheres*, Biotechnology, vol. 8, pp. 755–758 (1990).

Hsiao et al., *High–frequency transformation of yeast by plasmids containing the cloned yeast ARG4 gene*, Proceedings of the National Academy of Science, vol. 76, No. 8, pp. 3829–3833 (1979).

Igarashi et al., *An Immunodominant Haptenic Epitope of Carbamazepine Detected in Serum from Patents Given Long–Term Treatment with Carbamazepine Without Allergic Reaction*, Journal of Clinical Immunology, vol. 12, No. 5, pp. 335–340 (1992).

Johnson et al., *A month–long effect from a single injection of microencapsulated human growth hormone*, Nature Medicine, vol. 2, No. 7, pp. 795–799 (1996).

Jones, *Proteinase Mutants of Saccaromyces cerevisiae*, Genetics, vol. 85, No. 1, pp. 23–33 (1977).

Kelly et al., *Transformation of Aspergillus niger by the amdS gene of Aspergillus nidulans,* The Embro Journal, vol. 4, No. 2, pp. 475–479 (1985).

Keown et al., *Methods for Introducing DNA into Mammalian Cells*, Gene Expression Technology, vol. 185, pp. 527–537 (1990).

Kingsman et al., *Replication in Saccharomyces cerevisiae of plasmid pBR313 carrying DNA from the yeast trpl region*, Gene, vol. 7, No. 2, pp. 141–152 (1979).

Kyte et al., *A Simple Method for Displaying the Hydropathic Character of a Protein*, Journal of Molecular Biology, vol. 157, No. 1, pp. 105–132 (1982).

Lewis, *Controlled Release of Bioactive Agents from Lactide/Glycolide Polymers*, Biodegradable Polymers as Drug Delivery Systems, pp. 1–41 (1990).

Louvencourt et al., *Transformation of Kluyveromyces lactis by Killer Plasmid DNA*, Journal of Bacteriology, vol. 154, No. 2, pp. 737–742 (1983).

Mansour et al., *Disruption of the proto–oncogene int–2 in mouse embryo–derived stem cells: a general strategy for targeting mutations to non–selectable genes*, Nature, vol. 336, No. 6197, pp. 348–352 (1988).

Mantei et al., *Rabbit β–globin mRNA production in mouse L cells transformed with cloned rabbit β–globin chromosomal CAN*, Nature, vol. 281, No. 726, pp. 40–46 (1979).

Mather, *Establishment and Charterization of Two Distinct Mouse Testicular Epithelial Cell Lines*, Biology of Reproduction, vol. 23, No. 1, pp. 243–251 (1980).

Merrifield, *Solid Phase Peptide Synthesis*, Journal of the American Chemical Society, vol. 85, pp. 2149–2154 (1963).

Mordenti et al., *The Use of Interspecies Scaling in Toxicokinestics*, Toxicokinetics and New Drug Development, pp. 42–96 (1989).

Shaw et al., *A general method for the transfer of cloned genes to plant cells*, Gene, vol. 23, No. 3, pp. 315–330 (1983).

Sojar et al., *A Chemical Method for the Deglycosylation f Proteins*, Archives of Biochemistry and Biophysics, vol. 259, No. 1, pp. 52–57 (1987).

Sreekrishna et al., *High level expression of heterologous proteins in methylotrophic yeast*, Journal of Basic Microbiology, vol. 28, No. 4, pp. 265–278 (1988).

Stinchcomb et al., *Isolation and characterization of a yeast chromosomal replicator*, Nature, vol. 282, No. 5734, pp. 39–43 (1979).

Thotakura et al. *Enzymatic Deglycosylation of Glycoproteins*, Complex Carbohydrates, vol. 138, pp. 350–359 (1987).

Tilburn et al., *Transformation by integration in Aspergillus nidulans*, Gene, vol. 26, pp. 205–221 (1983).

Tschumper et al., *Sequence of a yeast DNA fragment containing a chromosomal replicator and the TRPI gene*, Gene, vol. 10, No. 2, pp. 157–166 (1980).

Urlaub et al., *Isolation of Chinese hamster cell mutants deficient in dihydrofolate reductase activity,* Proceedings of the National Academy of Sciences, vol. 77, No. 7, pp. 4216–4220 (1980).

van Solingen et al., *Fusion of Yeast Spheroplasts,* Journal of Bacteriology, vol. 130, No. 2, pp. 946–947 (1997).

Wells et al., *Importance of hydrogen–bond formation in stabilizing the transition state of subtilisin,* Philosophical Transactions of the Royal Society of London, Series A, Mathematical and Physical Sciences, vol. 317, pp. 415–423 (1986).

Wells et al., *Cassette Mutagenesis: an efficient method for generation of multiple mutations at defined sites,* Gene, vol. 34, pp. 315–323 (1985).

Yelton et al., *Transformation of Aspergillus nidulans by using a trpC plasmid,* Proceedings of the National Academy of Sciences, vol. 81, No. 5, pp. 1470–1474 (1984).

Zoller et al., *Oligonucleotide–directed mutagenesis using M13–derived vectors: and efficient and general procedure for the production of point mutations in any fragment of DNA,* Nucleic Acids Research, vol. 10, No. 20, pp. 6487–6500 (1982).

Hobby et al., *Identification of an Immunodominant Region Recognized by Human Autoantibodies in a Three–Dimensional Model of Thyroid Peroxidase,* Endocrinology 141:2018–2026 (2000).

Jaume et al., *Evidence for Genetic Transmission of Thyroid Peroxidase Autoantibody Epitopic "Fingerprints",* Journal of Clinical Endocrinology 84:1424–1431 (1999).

Jones, *Analysis of Autoimmunity Epitopes on Human Thyroid Peroxidase,* Autoimmunity vol. 30: 157–169 (1999).

McIntosh et al., *Molecular Analysis of the Antibody Response to Thyroglobulin and Thyroid Peroxidase,* Thyroid vol. 7:471–487 (1997).

Nishikawa et al., *The Quest for the Autoantibody Immunodominant Region on Thyroid Peroxidase: Guided Mutagenesis Based on a Hypothetical Three–Dimensional Model,* Endocrinology 137:1000–1006 (1996).

* cited by examiner

Thrombopoietin (TPO) principle megakaryocyte maturation and platelet production factor

FIG. 7

1 melteIllvv mllltarltl sspappacdl rvlskllrds hvlhsrlsqc pevhplptpv 61 llpavdfslg ewktqmeetk aqdilgavtl llegvmaarg qlgptclssl lgqlsgqvrl 121 llgalqsllg tqlppqgrtt ahkdpnaifl sfqhllrgkv rflmlvggst lcvrrapptt 181 avpsrtslvl tlnelpnrts glletnftas arttgsgllk wqqgfrakip gllnqtsrsl 241 dqipgylnri hellngtrgl fpgpsrrtlg apdissgtsd tgslppnlqp gyspspthpp 301 tgqytlfplp ptlptpvvql hpllpdpsap tptptsplln tsythsqnls qeg

SEQUENCE LISTING

```
<160> NUMBER OF SEQ ID NOS: 13

<210> SEQ ID NO 1
<211> LENGTH: 15
<212> TYPE: PRT
<213> ORGANISM: Homo sapiens

<400> SEQUENCE: 1

Leu Asn Thr Ser Tyr Thr His Ser Gln Asn Leu Ser Gln Glu Gly
1               5                   10                  15

<210> SEQ ID NO 2
<211> LENGTH: 20
<212> TYPE: PRT
<213> ORGANISM: Homo sapiens

<400> SEQUENCE: 2

Thr Pro Thr Ser Pro Leu Leu Asn Thr Ser Tyr Thr His Ser Gln Asn
1               5                   10                  15
```

Leu Ser Gln Glu
        20

<210> SEQ ID NO 3
<211> LENGTH: 17
<212> TYPE: PRT
<213> ORGANISM: Homo sapiens

<400> SEQUENCE: 3

Arg Ala Pro Pro Thr Thr Ala Val Pro Ser Arg Thr Ser Leu Val Leu
1               5                   10                  15

Thr

<210> SEQ ID NO 4
<211> LENGTH: 16
<212> TYPE: PRT
<213> ORGANISM: Homo sapiens

<400> SEQUENCE: 4

Pro Asn Arg Thr Ser Gly Leu Leu Glu Thr Asn Phe Thr Ala Ser Ala
1               5                   10                  15

<210> SEQ ID NO 5
<211> LENGTH: 17
<212> TYPE: PRT
<213> ORGANISM: Homo sapiens

<400> SEQUENCE: 5

Ser Gly Leu Leu Lys Trp Gln Gln Gly Phe Arg Ala Lys Ile Pro Gly
1               5                   10                  15

Leu

<210> SEQ ID NO 6
<211> LENGTH: 17
<212> TYPE: PRT
<213> ORGANISM: Homo sapiens

<400> SEQUENCE: 6

Ser Leu Asp Gln Ile Pro Gly Tyr Leu Asn Arg Ile His Glu Leu Leu
1               5                   10                  15

Asn

<210> SEQ ID NO 7
<211> LENGTH: 16
<212> TYPE: PRT
<213> ORGANISM: Homo sapiens

<400> SEQUENCE: 7

Ser Arg Arg Thr Leu Gly Ala Pro Asp Ile Ser Ser Gly Thr Ser Asp
1               5                   10                  15

<210> SEQ ID NO 8
<211> LENGTH: 11
<212> TYPE: PRT
<213> ORGANISM: Homo sapiens

<400> SEQUENCE: 8

Ser Asp Thr Gly Ser Leu Pro Pro Asn Leu Gln
1               5                   10

<210> SEQ ID NO 9
<211> LENGTH: 16

-continued

<212> TYPE: PRT
<213> ORGANISM: Homo sapiens

<400> SEQUENCE: 9

Gln Pro Gly Tyr Ser Pro Ser Pro Thr His Pro Pro Thr Gly Gln Tyr
1               5                   10                  15

<210> SEQ ID NO 10
<211> LENGTH: 16
<212> TYPE: PRT
<213> ORGANISM: Homo sapiens

<400> SEQUENCE: 10

Val Val Gln Leu His Pro Leu Leu Pro Asp Pro Ser Ala Pro Thr Pro
1               5                   10                  15

<210> SEQ ID NO 11
<211> LENGTH: 31
<212> TYPE: DNA
<213> ORGANISM: Homo sapiens

<400> SEQUENCE: 11
atcgatatcg atagccagac accccggcca g                                    31

<210> SEQ ID NO 12
<211> LENGTH: 33
<212> TYPE: DNA
<213> ORGANISM: Homo sapiens

<400> SEQUENCE: 12
agtcgacgtc gacgtcggca gtgtctgaga acc                                  33

<210> SEQ ID NO 13
<211> LENGTH: 353
<212> TYPE: PRT
<213> ORGANISM: Homo sapiens
<220> FEATURE:
<221> NAME/KEY: SIGNAL
<222> LOCATION: (1)..(21)
<223> OTHER INFORMATION:

<400> SEQUENCE: 13

Met Glu Leu Thr Glu Leu Leu Val Val Met Leu Leu Thr Ala
1               5                   10                  15

Arg Leu Thr Leu Ser Ser Pro Ala Pro Pro Ala Cys Asp Leu Arg Val
                20                  25                  30

Leu Ser Lys Leu Leu Arg Asp Ser His Val Leu His Ser Arg Leu Ser
            35                  40                  45

Gln Cys Pro Glu Val His Pro Leu Pro Thr Pro Val Leu Leu Pro Ala
        50                  55                  60

Val Asp Phe Ser Leu Gly Glu Trp Lys Thr Gln Met Glu Glu Thr Lys
65                  70                  75                  80

Ala Gln Asp Ile Leu Gly Ala Val Thr Leu Leu Leu Glu Gly Val Met
                85                  90                  95

Ala Ala Arg Gly Gln Leu Gly Pro Thr Cys Leu Ser Ser Leu Leu Gly
            100                 105                 110

Gln Leu Ser Gly Gln Val Arg Leu Leu Leu Gly Ala Leu Gln Ser Leu
        115                 120                 125

Leu Gly Thr Gln Leu Pro Pro Gln Gly Arg Thr Thr Ala His Lys Asp
    130                 135                 140

Pro Asn Ala Ile Phe Leu Ser Phe Gln His Leu Leu Arg Gly Lys Val

-continued

```
            145                 150                 155                 160
        Arg Phe Leu Met Leu Val Gly Gly Ser Thr Leu Cys Val Arg Arg Ala
                        165                 170                 175
        Pro Pro Thr Thr Ala Val Pro Ser Arg Thr Ser Leu Val Leu Thr Leu
                        180                 185                 190
        Asn Glu Leu Pro Asn Arg Thr Ser Gly Leu Leu Glu Thr Asn Phe Thr
                    195                 200                 205
        Ala Ser Ala Arg Thr Thr Gly Ser Gly Leu Leu Lys Trp Gln Gln Gly
                    210                 215                 220
        Phe Arg Ala Lys Ile Pro Gly Leu Leu Asn Gln Thr Ser Arg Ser Leu
        225                 230                 235                 240
        Asp Gln Ile Pro Gly Tyr Leu Asn Arg Ile His Glu Leu Leu Asn Gly
                        245                 250                 255
        Thr Arg Gly Leu Phe Pro Gly Pro Ser Arg Arg Thr Leu Gly Ala Pro
                        260                 265                 270
        Asp Ile Ser Ser Gly Thr Ser Asp Thr Gly Ser Leu Pro Pro Asn Leu
                    275                 280                 285
        Gln Pro Gly Tyr Ser Pro Ser Pro Thr His Pro Pro Thr Gly Gln Tyr
                    290                 295                 300
        Thr Leu Phe Pro Leu Pro Pro Thr Leu Pro Thr Pro Val Val Gln Leu
        305                 310                 315                 320
        His Pro Leu Leu Pro Asp Pro Ser Ala Pro Thr Pro Thr Pro Thr Ser
                        325                 330                 335
        Pro Leu Leu Asn Thr Ser Tyr Thr His Ser Gln Asn Leu Ser Gln Glu
                        340                 345                 350
        Gly
```

IDENTIFICATION AND MODIFICATION OF IMMUNODOMINANT EPITOPES IN POLYPEPTIDES

CROSS REFERENCE TO RELATED APPLICATION

This application claims benefit of U.S. Provisional Application Serial No. 60/243,913, filed Oct. 27, 2000, which application is incorporated herein by reference.

BACKGROUND OF THE INVENTION

A number of polypeptides from a variety of sources are used to treat disease in humans. If the polypeptide is derived from a heterologous or non-self source, patients readily develop an immune response to the polypeptide. In fact, in many cases, an immune response to the polypeptide is a desired therapeutic outcome. However, there are situations where an immune response to a polypeptide intended for therapeutic use is undesirable and could be very detrimental. For example, polypeptides intended for therapeutic use also include polypeptides that have endogenous or “self” counterparts. It is generally thought that an immune response is not generated to self or endogenous polypeptides, except in the case of autoimmune disease. If an immune response were generated upon administration of such polypeptides, adverse consequences could result including development of an autoimmune response.

Many factors contribute to immune responses to polypeptides. The presence of immunodominant epitopes in a polypeptide is one of the key factors in antibody responses. An immunodominant epitope is an epitope that more frequently elicits and binds to antibodies in a human or animal or population thereof when compared with other epitopes. Immunodominant epitopes in polypeptides are typically identified after administration of the polypeptide to the human or animal.

Immunodominant epitopes have been mapped on proteins using antibodies from treated animals. For example, staphylokinase is a bacterial polypeptide derived from *Staphylococcus aureus* and is used to treat myocardial infarction. Because staphylokinase is a heterologous or non-self polypeptide when administered to humans, treated patients readily develop an immune response to this polypeptide. This immune response can result in adverse reactions to further therapeutic treatment with the polypeptide. As described in U.S. Pat. No. 5,951,980, the immunodominant epitopes identified using antibodies from treated patients can be modified to reduce immunogenicity of the polypeptide.

In some cases, immunodominant epitopes on heterologous polypeptides have been masked or modified to shift the immune response to other epitopes in the polypeptide. As described in PCT 99/38978, patients exhibit antibody responses to IgG and IgE epitopes on allergens from heterologous sources such as peanuts, latex and food proteins. Once an IgE epitope is identified using the patient’s antibodies, the IgE epitope can be modified or masked to shift the immune response from the IgE epitope to other epitopes on the allergen. Similarly, the immune response to the immunodominant epitopes on pathogens, such as HIV, can be shifted to other epitopes on the pathogens by modifying or masking the immunodominant epitopes as described in U.S. Pat. No. 5,853,724. An immune response to these polypeptides is still a desired outcome.

Immunodominant epitopes have also been identified on some endogenous or self-proteins associated with autoimmune disease. Thyroid peroxidase is an endogenous molecule associated with autoimmune thyroid disease. For a review see McIntosh, R. S. et al, Thyroid 7:471 (1997). Immunodominant regions have been mapped on thyroid peroxidase using antibodies from patients with autoimmune disease. See Hobby, P. et al, Endocrinology 141:2018 (2000) and Nishikawa, et al, Endocrinology 137:1000 (1996). Mapping of these epitopes has been used to study the factors that might contribute to the development of autoimmune disease. See Jaume, J. C. et al, J. Clinical Endocrinology 84:1424 (1999). Factors that make self or endogenous polypeptides immunogenic in autoimmune disease are complex and not well understood.

Immunodominant epitopes on polypeptides intended for therapeutic use have not previously been identified before administration of these polypeptides to patients. In the case of polypeptides that have a sequence identical to all or a portion of a self or endogenous polypeptide, it was thought that these polypeptides would not elicit an immune response upon administration to patients.

One example of a recombinant human polypeptide used therapeutically is human thrombopoietin (TPO). A recombinant TPO has a sequence that is identical to a human thrombopoietin and is produced in CHO cells. TPO is an endogenous hemopoietic growth factor that stimulates proliferation and maturation of megakaryocytes and production of platelets. A recombinant human TPO is made up of 332 amino acids linked in a single polypeptide chain. Approximately in the middle of a molecule, there is a dibasic site of arginine 153 and arginine 154 that divide the molecule into a n-terminal and c-terminal epitopes. The n-terminal epitope is called the EPO epitope because of its similarity to erythropoietin or it is also called truncated TPO. The n-terminal epitope contains receptor-binding sites and represents the biologically active portion of the molecule. The c-terminal epitope is heavily glycosylated.

The major causes of thrombocytopenia in patients are impaired production of platelets by bone marrow, platelets sequestration in the spleen and destruction of platelets by autoimmune responses. Recombinant TPO stimulates production of platelets and is intended for the treatment of thrombocytopenia in patients undergoing chemotherapy. It is well known that repeated cycles of radiation and chemotherapy result in myelosuppression which limits dose intensity of chemotherapeutic agents. Administration of thrombopoietin, especially recombinant thrombopoietin, has resulted in improved tolerance of the patients for chemotherapy as described in WO 98/52598.

However, if administration of recombinant TPO or other therapeutic polypeptides can result in an immune response, patients may become refractory to the treatment or develop other adverse consequences. Thus a need exists to identify immunodominant epitopes in polypeptides intended for therapeutic use before administration to patients and to modify the polypeptides to reduce the immune response to the polypeptide.

SUMMARY OF THE INVENTION

One object of the present invention, is to develop methods to screen polypeptides intended for therapeutic use to identify immunodominant epitopes in order to reduce the chance of developing of an immune response to the polypeptide.

Another object of the invention is to design such polypeptides to modify the immunodominant epitopes in order to reduce the immune response to such polypeptides while retaining a substantial therapeutic activity when administered in vivo.

These and other objects will become apparent in the description in the embodiments of the invention provided herein.

The present invention is based on the unexpected and surprising finding that naive humans and animals can have pre-existing antibodies to a polypeptide intended for therapeutic use such as recombinant human polypeptides. It was also surprising that patients develop an antibody response after dosing or administration of these polypeptides because it was generally thought that an immune response would not be formed to a polypeptide having a sequence identical to that of the endogenous or self protein. These findings indicated a need to screen polypeptides intended for therapeutic use to identify immunodominant epitopes before administration to patients. The antibodies from naive patients with pre-existing antibodies to the polypeptide can advantageously be used to identify immunodominant epitopes on polypeptides before they are administered to patients. The identification of immunodominant epitopes prior to clinical application of the polypeptide can be used in designing less immunogenic molecules.

The invention provides for methods of identifying immunodominant epitopes in polypeptides, preferably polypeptides intended for therapeutic use. A method of the invention is a method for identifying at least one immunodominant epitope in a polypeptide by using an antibody or population of antibodies from a naive human or animal or population thereof. Immunodominant epitopes are those epitopes that more frequently bind to or are recognized by antibodies or a population of antibodies than other epitopes in the polypeptide. Immunodominant epitopes are also identified using both an antibody and a population of antibodies from a naive human or animal and an antibody or population thereof from a human or animal dosed with the polypeptide. An immunodominant epitope is selected for modification. The polypeptide is preferably a recombinant polypeptide intended for therapeutic use with a sequence identical to all or a portion of the native sequence of an endogenous polypeptide. The animal is preferably human.

Immunodominant epitopes are also identified by utilizing methods of predicting epitopes in polypeptides through the use of, for example, algorithms. Predicting epitopes in polypeptides reduces the amount of time and resources needed to identify immunodominant epitopes. Accordingly, a method of the invention involves providing a data set of the polypeptide, analyzing the data set with an algorithm to identify at least one predicted epitope in the polypeptide, and determining whether the predicted epitope is an actual immunodominant epitope.

The invention also provides for methods of modifying a polypeptide to reduce an immune response to the polypeptide while retaining a substantial therapeutic activity. A method involves identifying at least one immunodominant epitope in a polypeptide by using an antibody or population of antibodies from a naive human or animal or population thereof and/or an antibody or population of antibodies from a dosed human or animal, and modifying the epitope to reduce the immune response to the polypeptide while still retaining a substantial therapeutic activity. The modified polypeptides are useful therapeutically.

The invention also includes methods and compositions useful to make modified polypeptides. The methods include a method of making a modified polypeptide recombinantly by modifying a nucleic acid sequence to encode a modified polypeptide, wherein the modified polypeptide has at least one change to an immunodominant epitope to reduce the immune response to the polypeptide while still retaining a substantial therapeutic activity. Compositions include modified nucleic acids and host cells comprising the modified nucleic acids.

BRIEF DESCRIPTION OF THE DRAWINGS

FIG. 1 shows the structure of full-length recombinant human TPO (TPO FL) and truncated TPO (TPO TR);glycosylation sites are shown on C terminal.

FIG. 2 shows the effect of administration of rhesus thrombopoietin on platelet levels in normal rhesus monkeys. Antibody responses to rh TPO were also measured over time.

FIG. 3 shows the effect on platelet counts of passive transfer of anti-TPO antibodies to CD-1 mice on platelet counts.

FIGS. 4A–4D show the correlation of rhesus post-treatment platelet levels with antibody levels as measured in the 4 different assays. FIG. 4A shows the correlation of platelet counts with the presence of antibodies to the full length TPO; FIG. 4B shows the correlation of platelet counts with the presence of antibodies to the truncated TPO; FIG. 4C shows the correlation of platelet counts with the presence of antibodies that block binding of TPO to its receptor (c-mpl); and FIG. 4D shows the correlation of platelet counts with the presence of antibodies that inhibit proliferation of megakaryocytic HU3 cells.

FIG. 5 shows the competitive binding of rabbit anti-TPO peptide #19 in the presence of TPO peptides #15, #16, #19, #24 and #28.

FIG. 6 shows the competitive binding of human anti-TPO antibodies in the presence of increasing concentrations of rabbit anti-TPO peptide 15 antibodies.

FIG. 7 shows an amino acid sequence of recombinant human TPO (SEQ ID NO: 13).

DETAILED DESCRIPTION OF THE PREFERRED EMBODIMENT

Definitions

An "epitope" means a portion or a site on an antigen, such as a polypeptide, with the ability or potential to elicit and combine with an antibody. Polypeptides often include more than one epitope. For the purpose of this disclosure, a polypeptide epitope will usually include at least 3 amino acids, preferably 8 to 50 amino acids, and more preferably between about 10–20 amino acids in the peptide. There is no critical upper limit to the length of the peptide, which could comprise nearly the full length of the polypeptide sequence. Epitopes can be either linear or conformational epitopes. A linear epitope is comprised of a single segment of a primary sequence of a polypeptide chain. Linear epitopes can be contiguous or overlapping. Conformational epitopes are comprised of amino acids brought together by folding of the polypeptide to form a tertiary structure and the amino acids are not necessarily adjacent to one another in the linear sequence.

"Immunodominant epitope" means an epitope of a polypeptide that more frequently elicits or binds to antibodies from an antibody positive human or animal subject or population of thereof compared with other epitopes in the polypeptide. A polypeptide can have one or more immunodominant epitopes.

"Epitope specific or specificity" means the unique association between an antibody and its epitope. Epitope specificity is typically determined using competitive binding assays so that the enhanced binding between an antibody and its specific epitope is detected as compared to lower binding of the antibody to other epitopes.

"Immune response" is the development in an organism of a cellular and/or antibody mediated immune response to an antigen such as a polypeptide. Usually such a response includes but is not limited to one or more of the following: production of antibodies, B cells, helper T cells, suppressor T cells, and/or cytotoxic T cells. An immune response can be detected using any of several assays known to those with skill in the art. To "reduce the immune response" means that the immune response to the polypeptide or modified polypeptide is diminished. A reduced immune response can be determined by measuring the ability of the modified polypeptide to bind to an antibody to the polypeptide from an human or animal or population thereof as measured in a standard antibody-binding test such as an ELISA. If the modified polypeptide binds to the antibody with a lower affinity (preferably about 100 to 1000 fold decrease), the immune response to the polypeptide is reduced. The reduced immune response can also be measured by other methods such as determining whether an antibody response with substantially lower affinity is formed to the modified polypeptide upon administration to an animal.

"Immunogenicity" is the capacity of an antigen to stimulate an immune response.

"Naive" when used in conjunction with human or animal or population thereof means a human or animal or a population thereof that has no known previous administration or treatment with the polypeptide.

"Therapeutic" when used in conjunction polypeptide means a polypeptide intended for therapeutic use including prevention (prophylaxis), treatment, moderation, reduction and curing of symptoms of a disease or condition, "Therapeutic" when used in conjunction with activity means a biological activity of a polypeptide, preferably a biological activity which correlates with a therapeutic activity. Therapeutic activity when used in conjunction with thrombopoietin means having an in-vivo effector function which includes c-mpl binding, carrier binding activity, transduction of a proliferative signal including replication, DNA regulatory function, modulation of biological activity of other cytokines, receptor activation or regulation, and cell growth or differentiation.

"Not substantially inhibited" when used in conjunction with therapeutic activity means that a biological activity of the polypeptide as measured in an in vitro or in vivo assay is inhibited preferably no more than about 40 percent, or more preferably, no more than about 10 percent when compared to activity of the control. Inhibition of a biological activity of thrombopoietin can be measured by determining whether an antibody to an immunodominant epitope inhibits proliferation of HU3 megakaryocyte cell line in the presence of human thrombopoietin. Preferably, inhibition of no more than 40 percent, more preferably no more than 10 percent means the activity is not substantially inhibited.

"Retain a substantial therapeutic activity" when used in conjunction with a modified polypeptide means that the modified polypeptide has at least one biological activity and that the biological activity of a modified polypeptide is preferably about 60% or more of that of the unmodified polypeptide, more preferably about 90% or more than that of the unmodified polypeptide when measured in the same assay. This phrase also encompasses the situation where a biological activity of a modified polypeptide is enhanced over that of the unmodified or native sequence polypeptide.

"Endogenous or self" means a polypeptide, which is naturally occurring within an organism.

A "native sequence" polypeptide means a polypeptide having the same amino acid sequence of the polypeptide derived from nature and encompasses all naturally occurring forms of the polypeptide such as truncated forms, secreted forms, variant forms and naturally occurring allelic variants. A native sequence polypeptide can be isolated from nature or produced by recombinant or synthetic means. A native amino acid sequence for human thrombopoietin is provided in WO 95/18858.

"Recombinant polypeptide" means a polypeptide produced by the use of recombinant DNA techniques. Recombinant polypeptides include those polypeptides that have an endogenous counterpart and are, preferably produced in a non-human source. Recombinant polypeptides with an endogenous counterpart preferably have an amino acid sequence homologous to all or a portion of the native sequence of the endogenous polypeptide and most preferably, a sequence identical to all or a part of the native sequence. Human thrombopoietin (TPO) is an endogenous 332 amino acid polypeptide with a molecular weight of about 70-80 kd (as measured by SDS-PAGE). Thrombopoietin is a compound having thrombopoietic activity or being capable of increasing serum platelet counts in an animal. TPO is preferably capable of increasing endogenous platelet counts by at least 10% and preferably by 50%. A recombinant TPO has a sequence described in WO 98/52598 and can be produced according to the method of WO98/52598 in CHO cells.

"Homologous" means a biologically active polypeptide having at least 80% amino acid sequence identity with a full length native sequence polypeptide, a polypeptide lacking a signal peptide, an extra cellular domain of the polypeptide or any other fragment of the full length native sequence. Ordinarily, the polypeptide will have at least about 80% amino acid sequence identity, more preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity, and most preferably at least about 99% amino acid sequence identity with a full length native sequence polypeptide, a native sequence polypeptide lacking a signal peptide, an extra cellular domain of the polypeptide or any other fragment of the full length native sequence.

"Isolated" when used in combination with nucleic acid is a nucleic acid molecule that is identified and separated from at least one contaminate nucleic acid molecule with which it is associated in the natural source. An isolated nucleic acid molecule encoding a native sequence of human thrombopoietin is described in WO98/52598.

"Modified" means at least one change in an immunodominant epitope in a polypeptide and/or a nucleic acid encoding such a polypeptide. The change in the immunodominant epitope reduces an immune response to the polypeptide, especially the antibody response, while retaining a substantial therapeutic activity. Changes can include one or more deletions, additions, substitutions in an epitope, as well as chemical modifications to the amino acids in an epitope such as glycosylation, and pegylation of the amino acids.

"Percent (%) amino acid sequence identity" means the percentage of amino acid residues in a predicted epitope that are identical with amino acids in a known epitope or in a native sequence polypeptide compared to a homologous polypeptide, after aligning the sequence and introducing gaps, if necessary to achieve the maximum sequence identity, and not considering any conservative substitutions as part of the sequence identity. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Unless specifically stated otherwise, all % amino acid sequence identity values used herein are obtained as described above using the ALIGN-2 sequence comparison computer program. See WO 00/15796. However, % amino acid sequence identity may also be determined using the sequence comparison program NCBI-BLAST2 (Altschul et al., *Nucleic Acids Res.* 25:3389–3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A -2 (Altschul et al, Methods in Enzymology 266: 460–480 (1996)) and other programs available at protein sequence databases.

"Data set" when used herein means input data characterizing the polypeptide in a format useful in a computer implemented method to predict epitopes in the polypeptide. A data set of the polypeptide can be obtained from a number of sources including the linear sequence information of all or a part of the polypeptide and/or the conformational maps of all or a portion of the polypeptide. Linear sequence information of the polypeptide may be available from a database source such as Genbank, Protein Identification Resource Database, Swissprot and many others. Conformational epitopes can be identified by determining spatial conformation of amino acids by e.g., x-ray crystallography and 2-dimensional nuclear magnetic resonance. Information about secondary structure of polypeptides is also available on many databases such as Protein Identification Resource database and others. A data set of the polypeptide can be in a number of formats including a machine-readable format and/or in a format for propagation of a transmissible signal.

An increasing number of polypeptides are being used in a treatment of a variety of diseases. Some of those polypeptides are recombinant polypeptides with endogenous counterparts such as recombinant human thrombopoietin or recombinant human growth hormone. Because these recombinant polypeptides often have sequences identical to all or part of a native sequence of the endogenous counterparts, it was surprising to find that they can elicit antibodies in patients treated with the polypeptide. It is generally thought that an immune response is not typically generated to self or endogenous proteins. It was also surprising to find that some individuals having no known previous administration of or treatment with the polypeptide have preexisting antibodies to the recombinant polypeptide. These preexisting antibodies can advantageously be used to identify immunodominant epitopes in polypeptides before they are administered to patients. Immune responses to polypeptides, especially therapeutic polypeptides, can cause adverse effects upon administration of the polypeptides such as allergic responses, decreased therapeutic effectiveness of the polypeptide and potential auto immune disease.

In one aspect of the invention, polypeptides intended for therapeutic use are screened to identify immunodominant epitopes before they are administered to patients. Once the immunodominant epitopes are identified they can be modified to reduce an immune response to the polypeptide while still retaining a therapeutic activity of the polypeptide. Accordingly, the invention provides for methods of identifying immunodominant epitopes in a polypeptide and methods and compositions useful for modifying the polypeptides.

In another aspect, immunodominant epitopes are identified in polypeptides using an antibody or population of antibodies from a naive human or animal and an antibody or population of antibodies from a human or animal dosed with the polypeptide. Immunodominant epitopes identified using both sources of antibodies are selected for modification.

I. Methods of Identifying Immunodominant Epitopes in a Polypeptide.

A method of the invention provides for identifying immunodominant epitopes in a polypeptide so that the epitope can be modified to reduce the immune response to the polypeptide when administered in-vivo. A method involves identifying at least one immunodominant epitope in a polypeptide by using an antibody or population of antibodies from a naive human or animal subject or population thereof. Another method involves identifying an immunodominant epitope using an antibody or population from a naive human or animal and/or an antibody or population of antibodies from a dosed human or animal.

A. Polypeptides.

Polypeptides useful in the invention are those polypeptides that are intended for therapeutic use. Polypeptides include heterologous polypeptides from a source differing from the target animal species intended for therapeutic use, and polypeptides with endogenous counterparts in the same species targeted for therapeutic use. The polypeptides whether heterologous or having an endogenous counterpart are preferably produced in or obtained from a non-human cell.

Recombinant polypeptides can be produced in a variety of non-human host cells including prokaryote, yeast and higher eukaryote cells that are non-human. A number of different host cell types are described herein. Specific examples include *E. coli,* CHO cells, and *Sacchromyces cerevisiae.*

The preferred polypeptides are recombinant polypeptides that have an endogenous counterpart in a human such as human recombinant thrombopoietin. The polypeptides preferably have a sequence homologous to, or preferably identical to, all or a portion of a native sequence of the endogenous polypeptide. A polypeptide that has a sequence that is homologous to all or a portion of a native sequence is a biologically active polypeptide that preferably has at least about 80% sequence identity, more preferably at least about 95% amino acid sequence identity, more preferably at least about 96% amino acid sequence identity, more preferably at least about 97% amino acid sequence identity, more preferably at least about 98% amino acid sequence identity, and most preferably at least about 99% amino acid sequence identity with a full length native sequence polypeptide, a native sequence polypeptide lacking a signal peptide, an extra cellular domain of the polypeptide or any other fragment of the full length native sequence.

Polypeptides are preferably those intended for use in the treatment of cancer and/or patient undergoing chemotherapy or radiation treatment, in treating viral infections, metabolic disorders, and growth disorders. Polypeptides useful in such treatments include cytokines, antibodies (including human antibodies and humanized antibodies), receptors including soluble receptor fragments, enzymes, and growth factors.

Included among cytokines and growth factors are growth hormone, bovine growth hormone, insulin like growth factors, human growth hormone including n-methionyl human growth hormone, parathyroid hormone, thyroxine, insulin, proinsulin, amylin, relaxin, prorelaxin, glycoprotein hormones such as follicle stimulating hormone (FSH), leutinizing hormone (LH), hemapoietic growth factor, fibroblast growth factor, prolactin, placental lactogen, tumor necrosis factors, mullerian inhibiting substance, mouse gonadotropin -associated polypeptide, inhibin, activin, vascular endothelial growth factors, integrin, nerve growth factors such as NGF-beta, insulin-like growth factor-I and II, erythropoietin, osteoinductive factors, interferons, colony stimulating factors, interleukins, bone morphogenetic proteins, LIF,SCF,FLT-3 ligand and kit-ligand.

Chimeric antibodies are those antibodies that have at least a portion of heavy and light chains of the antibody molecule derived from different sources or species. Humanized antibodies are antibodies that have the variable or complementarity determining regions (CDR) derived from another animal species such as a mouse combined with the framework of the antibody molecule from a human. Antibodies or portions of antibodies can be isolated and/or derived from phagemid displays prepared from different species as described in U.S. Pat. Nos. 5,821,047; 5,969,108, and 5,872, 215. Other antibodies include human antibodies prepared using genetically engineered mice such as mice produced by Abgenix, Inc. and Medarex, Inc. Antibodies include full-length antibodies, single chain antibodies, monoclonal antibodies, polyclonal antibodies, multi-specific antibodies, and fragments of antibodies such as Fab, F(ab)2, and Fv fragments. Examples of humanized antibodies are recombinant humanized antibodies that bind to antigens such as CD-11a, HER2, CD 20, VEGF, IgE, IL-9, PSCA, PSMA, and MadCAM. The antigen CD-11a is found on T cells and the humanized antibody is intended for treatment of psoriasis.

The polypeptides are used therapeutically in a variety of animal species including human, primate, cattle, pigs, poultry and mice. The preferred species is human.

B. Identifying at least One Immunodominant Epitope in a Polypeptide.

Typically immunodominant epitopes are mapped on polypeptides after the polypeptide has been administered to the animal. In one aspect of the invention, it is desirable to identify immunodominant epitopes before the polypeptide is administered to the animal. Such epitopes can be identified by analyzing the antibody specificity of antibodies obtained from naive humans or animals that have had no known previous administration of or treatment with the polypeptide. Immunodominant epitopes identified in polypeptides by binding with antibodies from naive animals are predictive of the immune response to the polypeptides after dosing or administration of the polypeptide.

In accord with a method of the invention, at least one epitope in the polypeptide can be identified by characterizing the specificity of antibodies to the polypeptide that are obtained from a naive human subject or animal or populations thereof using standard methods such as direct and indirect ELISA assays, competitive binding assays, radioimmune assays, cell-based binding assays, and/or bioactivity assays as described in Current Protocols in Immunology, John Wiley and Sons, 2000.

Antibodies are preferably obtained from a human or animal or population thereof depending on the target for the intended therapeutic use. For example, a recombinant human thrombopoietin has a sequence identical to human thrombopoietin. Naive human subjects are then screened for pre-existing or preformed antibodies that bind to the recombinant human thrombopoietin. The antibodies that bind to the polypeptide can be derived from a single human or animal subject or pooled from a population of subjects.

The antibodies are also optionally be screened to determine whether the antibodies inhibit a therapeutic activity of the polypeptide. The bioactivity assays can be conducted in-vivo or in-vitro. The type of assay selected will depend upon the polypeptide and its therapeutic activities. Such assays are known to those of skill in the art and can be readily identified and selected. Antibodies that do not substantially inhibit a therapeutic activity of the polypeptide are those antibodies that preferably do not inhibit a therapeutic activity of the polypeptide no more than about 40% and more preferably no more than about 10%. Alternatively, if information about the regions of the polypeptide that provide for the biological activities of the polypeptide are known, then immunodominant epitopes not located in those regions can optionally be selected for modification. Regions or domains that provide for therapeutic function of some polypeptides are known to those of skill in the art.

Epitope specificity of the antibodies are determined using standard methods including methods of mapping epitopes such as described in *Epitope Mapping Protocols in Molecular Biology*, vol. 66 (Glenn E. Morris, ed., 1996) Humana Press Totowa, N.J.

One such method involves generating a number of antibodies that are specific for linear epitopes. The linear epitopes are preferably about 3 to 20 amino acids long, more preferably about 8 to 20 amino acids long and have a sequence that is identical to the linear sequence of the polypeptide. Antibodies are generated to these known epitopes using standard methods and include polyclonal, monoclonal, fragments of antibodies such as F(ab) or F(ab)$_2$, and antibodies that are tagged or derivatized for easy detection. The specificity of each of the antibodies will be to a known linear epitope.

The epitope specificity of the antibody obtained from a human subject can be determined in competitive inhibition assays. An antibody that can completely competitively inhibit the binding of an antibody to its known epitope is also specific for that epitope.

Alternatively, conformational epitopes can be mapped using molecular modeling techniques. A three dimensional structure of the polypeptide can be developed from x ray crystallography or 2-dimensional NMR or by comparison to other homologous polypeptides. Peptides that are located on the surface in the three-dimensional structure can be synthesized and tested for reactivity with antibodies from a human or animal subject.

Once at least one epitope that binds to an antibody from a naive human or animal subject or population thereof is identified, then an immunodominant epitope is identified. An immunodominant epitope is identified by determining whether the epitope binds more frequently to an antibody or population of antibodies in a human or animal subject or a population thereof when compared to other epitopes. An immunodominant epitope can be the only epitope that can be found to bind to the antibodies from a human subject or population thereof or a polypeptide can have more than one immunodominant epitope.

Preferably, an immunodominant epitope in the polypeptide recognized by antibodies from a naive human or animal is also recognized by antibodies formed in a human or animal or population thereof after dosing with the polypeptide. Dosing means administration or treatment of a human or animal with the polypeptide. Immunodominant epitopes including epitopes recognized both by antibodies from a naive human or animal and a dosed human or animal are selected for modification. Immunodominant epitopes that are identified by binding to naive antibodies are predictive of the antibodies formed in response to dosing or administration of the polypeptide. Polypeptides have been administered therapeutically and an immune response developed to that polypeptide. Analysis of the epitope specificity of the antibodies developed in a human or animal subject that has been dosed with the polypeptide confirm the prediction of immunodominant epitopes identified in the polypeptide using antibodies from naive animals or using algorithms. Preferably, the immunodominant epitope selected to be modified is an immunodominant epitope recognized by antibodies from both sources.

C. Immunodominant Epitope of Human Thrombopoietin.

An immunodominant epitope on human thrombopoietin was identified using the method described herein. Human patients with no known previous dosing or administration of recombinant human thrombopoietin were screened for antibodies to both the full length and truncated human thrombopoietin in an ELISA assay as described in Example 2. Antibodies positive for binding to human thrombopoietin in the ELISA assay were then screened in bioactivity assays for the ability to block binding of human thrombopoietin to the c-mpl receptor or inhibit proliferation of the HU3 megakaryocytes cell line as described in Example 2. Antibodies that did not substantially inhibit a therapeutic activity of the human thrombopoietin were selected.

The epitope specificity of the antibody was determined using standard linear epitope mapping techniques. The epitope was identified as an immunodominant epitope by using antibodies to human thrombopoietin obtained from human subjects that had not previously been dosed with human thrombopoietin. Antibodies from human subjects dosed with human recombinant thrombopoietin also bound to the same epitope.

An immunodominant epitope of human thrombopoietin includes amino acids 318 to 332 and has the followings sequence (represented in single letter code):

LNTSYTHSQNLSEQ (SEQ ID NO: 1)

D. Methods of Predicting Immunodominant Epitopes.

It is also useful to predict immunodominant epitopes in a polypeptide so that the polypeptide can be modified before it is administered in-vivo. If the immunodominant epitopes of the polypeptide are predicted, the amount of work necessary to identify the actual immunodominant epitopes in the polypeptide can be substantially reduced. A method for predicting an epitope includes providing a data set of the polypeptide, analyzing the data set with an algorithm to provide predicted epitopes and determining whether the predicted epitope is an actual immunodominant epitope in an human or animal or population thereof.

A data set of the polypeptide can be obtained from a number of sources and includes the linear sequence information of all or a part of the polypeptide and/or the conformational maps of all or a portion of the polypeptide. Linear sequence information of the polypeptide may be available from a database source such as Genbank, Protein Identification Resource Database, Swissprot and many others. Conformational epitopes can be identified by determining spatial conformation of amino acids by e.g., x-ray crystallography and 2-dimensional nuclear magnetic resonance. Information about secondary structure of polypeptides is also available on many databases such as Protein Identification Resource database and others. A data set of the recombinant polypeptide can be in a number of formats including a machine-readable format and/or in a format for propagation of a transmissible signal.

A data set of the polypeptide can be analyzed using different algorithms known to those of skill in the art and/or commercially available to provide predicted epitopes in polypeptides. Computer programs that are available to evaluate the secondary structure of polypeptides are described in U.S. Pat. No. 5,940,307. For example, computer algorithms that formulate hydropathy scales from the amino acid sequence of the protein utilizing the hydrophobic and hydrophilic properties of the amino acids can also be used according to the Kyte and Doolittle method. See Kyte and Doolittle, J. Mol. Biol.157:105 (1982). Points of highest local average of hydrophilicities are indicative of epitopes of the polypeptide. Polypeptides can also be analyzed to predict immunodominant epitopes using commercially available services such as provided by Epivax, Inc. of Providence, R.I. The preferred algorithms are those that predict the epitopes that bind to Class II MHC molecules.

Analysis of a data set of the polypeptide with such algorithms provides predicted epitopes. The predicted epitopes are used to make peptides prepared by standard methods of automated peptide synthesis or recombinant DNA techniques.

Peptides with a sequence of the predicted epitopes are analyzed to determine if one or more of these epitopes is an immunodominant epitope. One method for determining whether such a predicted epitope is also an immunodominant epitope is to compare the amino acid sequence of the predicted epitope with the amino acid sequence of known epitopes(if that information is available) in the polypeptide using standard methods to determine the percent identity between the two sequences. If the predicted epitope has a percent sequence identity of about 50% or more, preferably about 75% or more with a known epitope of the polypeptide, then this epitope is selected for further analysis and/or modification.

Alternatively, the predicted epitope is identified as an actual immunodominant epitope by determining whether a peptide with the sequence of the predicted epitope binds to an antibody or population of antibodies from a naive human or animal subject and/or an antibody or population of antibodies from a dosed human or animal subject using standard methods such as an ELISA or competitive binding assay. If a peptide with the sequence of the predicted epitope binds to an antibody to the polypeptide from a human or animal subject then it is an actual epitope. Whether the predicted epitope is an immunodominant epitope can be determined if that epitope is found more often to bind to antibodies in an human or animal or population thereof when compared to other epitopes in the polypeptide.

Optionally, the predicted epitopes are also further screened for those epitopes that bind to antibodies that do not substantially inhibit a therapeutic activity of the polypeptide. If a peptide with the sequence of a predicted epitope binds to an antibody to the polypeptide obtained from a human subject or an animal, then the ability of that antibody to inhibit a therapeutic activity of the endogenous polypeptide can be measured. Epitopes that bind to or are recognized by antibodies that do not substantially inhibit a therapeutic activity of the polypeptide can optionally be selected. Alternatively, if information about the regions or domains of the polypeptide that provide for the biological activities of the polypeptide is known, then predicted immunodominant epitopes not located in those regions can optionally be selected for further analysis.

Once immunodominant epitopes are predicted or identified using an algorithm, such as provided by Epivax, Inc., the predicted epitopes are optionally also scored for the likelihood of binding to HLA DR and DQ alleles. This information provides an indication of how widespread this immunodominant epitope is recognized in the population. Optionally, immunodominant epitopes that are recognized across a number of HLA types when compared with other epitopes identified in the polypeptide are selected for modification. The scoring information provided from Epivax can be used to identify the likelihood of binding to HLA alleles and the frequency that those alleles are found in the population can be determined by referring to tables provided by Bone Marrow Donor registries or the International Histocompatibility Working Group.

Analysis of the amino acid sequence of human thrombopoietin resulted in the identification of a predicted immunodominant epitope using the service provided by Epivax, Inc. Fourteen out of 15 amino acid residues of the immunodominant peptide identified using antibodies from naive patients showed 100% homology with the 14 residues at the C-terminal of the 20 amino acid region predicted by EpiVax.

The sequence of the predicted immunodominant epitope has an amino acid sequence identical to amino acid residues 312 to 331:

TPTSPLLNTSYTHSQNLSQE (SEQ ID NO: 2)

The epitope or site identified above was found to include a motif that is likely to bind to 11 HLA DR and DQ alleles. These alleles are found in 42.2% Native Americans, 37.3% Caucasians, 26.6% African Americans, and 23.7% Asian Americans.

II. Methods of Modifying a Polypeptide

The invention also provides methods and compositions for modifying a polypeptide so as to reduce the immune response to the polypeptide when administrated in-vivo while retaining a therapeutic activity of the polypeptide. The polypeptide is preferably modified before it is administered in-vivo.

A method of modifying a polypeptide involves identifying at least one immunodominant epitope in the polypeptide using the methods as described herein, and modifying the immunodominant epitope to decrease the immune response to the polypeptide while still retaining substantial therapeutic activity of the polypeptide.

A. Modifications to Immunodominant Epitopes

Modifications to an immunodominant epitope are made by making at least one change to the amino acids in the immunodominant epitope. Modifications to amino acids include deleting all or a portion of the epitope, substituting at least one or more amino acids in the epitope, and inserting amino acids in the epitope. In addition, one or more amino acid residues of the epitope can also be modified to mask the epitope by modifications to the amino acids such as N-glycosylation, pegylation, and the like. Multiple modifications can be made in a single immunodominant epitope. Modifications are preferably made in all immunodominant epitopes if more than one immunodominant epitope is present in the polypeptide.

Modifications are made to change one or more amino acids in the immunodominant epitope so as to reduce the immunogenicity of that epitope. The modifications are preferably those that do not significantly alter the overall tertiary structure of the polypeptide. Examples of preferred modifications include modifications that can be made to change the ability of the epitope to bind to Class II MHC molecules. Modifications known to those of skill in the art for changing the binding of an epitope to a Class II MHC molecule include changing a c-terminal hydrophobic anchor residue to a residue that is hydrophilic, and/or changing a negatively charged amino acid residue at the n-terminal of the epitope to one that is neutral or positively charged. Alternatively, substitutions can be made to reduce the local average hydrophilicity as determined using the Kyte and Doolittle method discussed supra. It is known to those with skill in the art that a high local average hydrophilicity value is one identifying characteristic of an antigen or an epitope. Other changes that will impact the ability of the epitope to bind to a Class II MHC molecule can also be made. The changes include deletions, substitutions, and insertions of amino acids in the epitope.

Modified polypeptides are prepared by introducing appropriate nucleotide changes into the DNA encoding the polypeptide, and/or by synthesis of the desired polypeptide. Preferably, the polypeptide has a sequence identical to all or a portion of a native amino acid sequence of an endogenous polypeptide. Amino acid sequences of polypeptides may be obtained in protein sequences databases such as Genbank, Protein Identification Resource database and others. Those skilled in the art will appreciate that amino acid changes may alter post-translational processes of the polypeptide, such as changing the number or position of glycosylation sites or altering the membrane anchoring characteristics.

Modifications in the sequence polypeptide or in various epitopes of the polypeptide described herein, can be made, for example, using any of the techniques and guidelines for conservative and non-conservative mutations set forth, for instance, in U.S. Pat. No. 5,364,934. Modifications may be a substitution, deletion or insertion of one or more codons encoding the polypeptide that results in a change in the amino acid sequence of the polypeptide.

Optionally, the variation is by substitution of at least one amino acid with any other amino acid in one or more of the epitopes of the polypeptide. Guidance in determining which amino acid residue may be inserted, substituted or deleted without adversely affecting the desired biological activity may be found by 1) identifying regions of the molecule that are known to be associated with a biological activity of the polypeptide and selecting changes that are not likely to affect the functional region and/or 2) identifying changes that will alter, preferably decrease, the binding of immunodominant epitopes to class II MHC molecules or antibodies from an antibody positive human or animal or population thereof.

Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The modification allowed or desired may be determined by systematically making insertions, deletions or substitutions of amino acids in the sequence and testing the resulting modified polypeptides for activity in comparison to that exhibited by the full-length or native sequence polypeptide including therapeutic activity and binding to an antibody specific for the polypeptide.

Fragment or truncated versions of the polypeptide are provided herein. Such fragments may be truncated at the N-terminus or C-terminus, or may lack internal residues, for example, when compared with a full-length polypeptide. Certain fragments lack amino acid residues that are not essential for a desired biological activity of the polypeptide but are lacking immunodominant epitopes.

Polypeptide fragments may be prepared by any of a number of conventional techniques. Desired peptide fragments may be chemically synthesized. An alternative approach involves generating polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, polypeptide fragments share at least one biological activity with the native polypeptide.

In particular embodiments, conservative substitutions of interest are shown in Table 1 under the heading of preferred substitutions. If such substitutions result in a reduction of the binding of the polypeptide to an antibody from a naive human or animal or population thereof, then more substantial changes, denominated exemplary substitutions in Table 1, or as further described below in reference to amino acid classes, are introduced and the products screened for binding to antibodies to the polypeptide and for therapeutic activity.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in immunological identity of the polypeptide can also be accomplished by selecting substitutions that differ significantly in their effect on maintaining (a) the structure of the polypeptide backbone in the area of the substitution, for example, as a sheet or helical conformation, (b) the charge or hydrophobicity of the molecule at the immunodominant epitope, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The modifications can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the DNA encoding a modified polypeptide.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081–1085 (1989)]. Alanine is also typically preferred because it is the most common amino acid. Further, it is frequently found in both buried and exposed positions [Creighton, *The Proteins*, (W. H. Freeman & Co., N.Y.); Chothia, *J. Mol. Biol.*, 150:1 (1976)]. If alanine substitution does not yield adequate amounts of modified polypeptide, an isoteric amino acid can be used.

Covalent modifications of polypeptide, preferably those that mask an immunodominant epitope, are included within the scope of this invention. A type of covalent modification of the polypeptide included within the scope of this invention comprises altering the native glycosylation pattern of the polypeptide. "Altering the native glycosylation pattern" is intended for purposes herein to mean deleting one or more carbohydrate moieties found in native sequence polypeptide (either by removing the underlying glycosylation site or by deleting the glycosylation by chemical and/or enzymatic means), and/or adding one or more glycosylation sites that are not present in the native sequence polypeptide. In addition, the phrase includes qualitative changes in the glycosylation of the native proteins, involving a change in the nature and proportions of the various carbohydrate moieties present.

Addition of glycosylation sites to the polypeptide may be accomplished by altering the amino acid sequence. The alteration may be made, for example, by the addition of, or substitution by, one or more serine or threonine residues to the native sequence polypeptide (for O-linked glycosylation sites). The polypeptide amino acid sequence may optionally be altered through changes at the DNA level, particularly by mutating the DNA encoding the polypeptide at preselected bases such that codons are generated that will translate into the desired amino acids.

Another means of increasing the number of carbohydrate moieties in the polypeptide is by chemical or enzymatic coupling of glycosides to the polypeptide. Such methods are described in the art, e.g., in WO 87/05330 published Sept. 11, 1987, and in Aplin and Wriston, *CRC Crit. Rev. Biochem.*, pp. 259–306 (1981).

Removal of carbohydrate moieties present in the polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.* 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of polypeptide comprises linking the polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the -amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

The modified polypeptide of the present invention may also be in the form of a chimeric molecule comprising polypeptide fused to another, heterologous polypeptide or amino acid sequence.

Once a particular modification to an immunodominant epitope is selected, modified polypeptides are prepared by standard methods including recombinant DNA technology as described herein. Modified polypeptides are produced and are screened to determine whether such a polypeptide will have reduced immunogenicity. There are a number of methods for determining whether any modification made to the polypeptide results in reduced immune response. One method for making such a determination is to determine whether the modified polypeptide has reduced binding to antibodies to the polypeptide, preferably an antibody from a naive human subject or population thereof and/or to antibodies from a human or animal dosed with the polypeptide. If the modified polypeptide has reduced binding, preferably about a 100 to 1000 fold decrease in affinity, to antibodies to the polypeptide from such a human subject, then it is a polypeptide, which has reduced immunogenicity.

Another method for determining whether the modified polypeptide has reduced immunogenicity is to administer the modified polypeptide to an animal to see if any immune response develops to the modified polypeptide. Animal models include SCID/Hu animals which have all or a part of the human immune system grafted into a an immunodeficient animal. Administration of the modified polypeptide to such an animal model indicates whether an immune reponse is generated to the modified polypeptide. Alternatively, if a treated or dosed population of humans or animals exist, antibodies formed to the polypeptide are used to determine if the modified polypeptide will bind to those antibodies. Modified polypeptides which induce no antibody response at all, induce antibodies with lower affinity, preferably about 100 to 1000 fold lower affinity (when compared to the antibodies to the un modified polypeptide), or have reduced binding to antibodies from naive or dosed animals have reduced immunogenicity. Any one or all of the above methods can be utilized to screen any of the modified polypeptides to determine whether such a peptide has reduced immunogenicity.

The modified polypeptide is also screened to determine if the modification affects a biologic or therapeutic activity of the polypeptide. The modified polypeptide retains substantially the same therapeutic activity of the unmodified polypeptide, preferably about 60% or more and more preferably about 90% or more of the activity of the unmodified polypeptide. The modified polypeptide can also have a biological activity that is enhanced compared to an unmodified or native sequence polypeptide. The modified polypeptide can be assayed for biological activity, preferably a biological activity that correlates with a therapeutic activity. The assay selected will depend in the polypeptide and the desired therapeutic use. Therapeutic activity assays are known to those with skill in the art.

B. Methods of Making a Modified Polypeptide

Methods of making modified polypeptides are known to those with skill in the art and include recombinant DNA techniques. A number of polypeptides have been produced by recombinant DNA techniques and therefore both nucleic acid and amino acid sequences for these polypeptides are known. Reference can be made to Genbank and other databases for both nucleotide and amino acid sequence information. Methods for isolating nucleic acid sequences encoding polypeptides are standard and are described in many references including Sambrook et al, Molecular Cloning: a Laboratory Manual, Cold Spring Harbor, N.Y. (1989).

Modifications to the amino acid sequence can be made by modifying a nucleic acid sequence encoding the polypeptide to encode a modified polypeptide. A particular modification to the amino acid sequence can be selected as described herein to form a modified polypeptide that has a reduced immune response while still retaining a functional activity.

The description below relates primarily to production of a modified polypeptide by culturing cells transformed or transfected with a vector containing a nucleic acid. It is, of course, contemplated that alternative methods, which are well known in the art, may be employed to prepare modified polypeptide. For instance, the modified polypeptide sequence, or portions thereof, may be produced by direct peptide synthesis using solid-phase techniques [see, e.g., Stewart et al., *Solid-Phase Peptide Synthesis*, W. H. Freeman Co., San Francisco, Calif. (1969); Merrifield, *J. Am. Chem. Soc.,* 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the modified polypeptide may be chemically synthesized separately and combined using chemical or enzymatic methods to produce the full-length modified polypeptide.

1. Isolation of DNA Encoding Polypeptide

DNA encoding a native sequence of the polypeptide may be obtained from a cDNA library prepared from tissue believed to possess the polypeptide mRNA and to express it at a detectable level. Accordingly, human polypeptide DNA can be conveniently obtained from a cDNA library prepared from human tissue. A gene encoding a native sequence of the polypeptide may also be obtained from a genomic library or by known synthetic procedures (e.g., automated nucleic acid synthesis).

Libraries can be screened with probes (such as antibodies to the native sequence of the polypeptide or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding a native sequence polypeptide is to use PCR methodology [Sambrook et al., supra; Dieffenbach et al., *PCR Primer: A Laboratory Manual* (Cold Spring Harbor Laboratory Press, 1995)].

A cDNA library can be screened as follows. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length native sequence can be determined using methods known in the art and as described herein.

Nucleic acid having protein coding sequence may be obtained by screening selected cDNA or genomic libraries using a deduced or known amino acid sequence and, if necessary, using conventional primer extension procedures as described in Sambrook et al., supra, to detect precursors and processing intermediates of mRNA that may not have been reverse-transcribed into cDNA.

2. Modification of a DNA Sequence to Encode a Modified Polypeptide

Once a DNA sequence encoding a native sequence of the polypeptide is isolated, it can be modified to encode a modified polypeptide with at least one change to an immunodominant epitope of the polypeptide. Changes are made to the nucleic acid sequence to alter the codons encoding the immunodominant epitope amino acids. The modifications to the nucleic acid sequence to accomplish these changes can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the DNA encoding a modified polypeptide.

3. Selection and Transformation of Host Cells

Host cells are transfected or transformed with expression or cloning vectors described herein for production of the modified polypeptides and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene,* 23:315 (1983) and WO 89/05859 published Jun. 29, 1989. For mammalian cells without such cell walls, the calcium phosphate precipitation method of Graham and van der Eb, *Virology,* 52:456–457 (1978) can be employed. General aspects of mammalian cell host system transfections have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyomithine, may also be used. For various techniques for transforming mammalian cells, see Keown et al., *Methods in Enzymology,* 185:527–537 (1990) and Mansour et al., *Nature,* 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as

*E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA ; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT kan$^r$; *E. coli* W3110 strain 37D6, which has the complete genotype tonA ptr3 phoA E15 (argF-lac) 169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for vectors encoding a modified polypeptide. *Saccharomyces cerevisiae* is a commonly used lower eukaryotic host microorganism. Others include *Schizosaccharomyces pombe* (Beach and Nurse, Nature, 290: 140 [1981]; EP 139,383 published May 2, 1985); Kluyveromyces hosts (U.S. Pat. No. 4,943,529; Fleer et al., Bio/Technology, 9:968–975 (1991)) such as, e.g., *K. lactis* (MW98-8C, CBS683, CBS4574; Louvencourt et al., J. Bacteriol., 154 (2):737–742 [1983]), *K fragilis* (ATCC 12,424), *K. bulgaricus* (ATCC 16,045), *K wickeramii* (ATCC 24,178), *K waltii* (ATCC 56,500), *K. drosophilarum* (ATCC 36,906; Van den Berg et al., Bio/Technology, 8:135 (1990)), *K. thermotolerans*, and *K. marxianus; yarrowia* (EP 402,226); *Pichia pastoris* (EP 183,070; Sreekrishna et al., J. Basic Microbiol., 28:265–278 [1988]); Candida; *Trichoderma reesia* (EP 244,234); *Neurospora crassa* (Case et al., Proc. Natl. Acad. Sci. USA, 76:5259–5263 [1979]); Schwanniomyces such as *Schwanniomyces occidentalis* (EP 394,538 published ) Oct. 31, 1990); and filamentous fungi such as, e.g., Neurospora, Penicillium, Tolypocladium (WO 91/00357 published Jan. 10, 1991), and Aspergillus hosts such as *A. nidulans* (Ballance et al., Biochem. Biophys. Res. Commun., 112:284–289 [1983]; Tilburn et al., Gene, 26:205–221 [1983]; Yelton et al., Proc. Natl. Acad. Sci. USA, 81: 1470–1474 [1984]) and *A. niger* (Kelly and Hynes, EMBO J., 4:475–479 [1985]). Methylotropic yeasts are suitable herein and include, but are not limited to, yeast capable of growth on methanol selected from the genera consisting of Hansenula, Candida, Kloeckera, Pichia, Saccharomyces, Torulopsis, and Rhodotorula. A list of specific species that are exemplary of this class of yeasts may be found in C. Anthony, *The Biochemistry of Methylotrophs*, 269 (1982).

Suitable host cells for the expression of glycosylated modified polypeptide are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); Chinese hamster ovary cells/-DHFR (CHO, Urlaub and Chasin, Proc. Natl. Acad. Sci. USA, 77:4216 (1980)); mouse sertoli cells (TM4, Mather, Biol. Reprod., 23:243–251 (1980)); and mouse mammary tumor (MMT 060562, ATCC CCL51). The selection of the appropriate host cell is deemed to be within the skill in the art.

4. Selection and Use of a Replicable Vector

The nucleic acid (e.g., cDNA or genomic DNA) encoding a modified polypeptide in accord with the invention may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The modified polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the DNA encoding the modified polypeptide that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the nucleic acid encoding a modified polypeptide, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the nucleic acid sequence encoding the modified polypeptide to direct mRNA synthesis. Promoters recognized by a variety of potential host cells are well known. Promoters suitable for use with prokaryotic hosts include the -lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21–25 (1983)]. Promoters for use in bacterial systems also will contain a Shine-Dalgarno (S.D.) sequence operably linked to the DNA encoding the modified polypeptide.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the modified polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, -fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the modified polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untransalated regions of eukaryotic or viral DNAs or cDNAs. These regions contain nucleotide segments transcribed as polyadenylated fragments in the untranslated portion of the mRNA encoding a modified polypeptide.

Still other methods, vectors, and host cells suitable for adaptation to the synthesis of a modified recombinant polypeptide in vertebrate cell culture are described in Gething et al., *Nature,* 293:620–625 (1981); Mantei et al., *Nature,* 281:40–46 (1979); EP 117,060; and EP 117,058.

5. Purification of a Modified Polypeptide

Forms of the modified polypeptide may be recovered from culture medium or from host cell lysates. Methods for purification of native sequence polypeptides known to those of skill in the art can be preferably employed for purification of the modified polypeptide. If membrane-bound, it can be released from the membrane using a suitable detergent solution (e.g. Triton-X 100) or by enzymatic cleavage. Cells employed in expression of modified polypeptide can be disrupted by various physical or chemical means, such as freeze-thaw cycling, sonication, mechanical disruption, or cell lysing agents.

It may be desired to purify modified polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the modified polypeptide. Various methods of protein purification may be employed and such methods are known in the art and described for example in Deutscher, *Methods in Enzymology,* 182 (1990); Scopes, *Protein Purification: Principles and Practice,* Springer-Verlag, New York (1982). The purification step(s) selected will depend, for example, on the nature of the production process used and the particular modified polypeptide produced.

6. Modified Human Thrombopoietin

A specific example of a modified polypeptide is a modified thrombopoietin having reduced immunogenicity while retaining substantial therapeutic activity. An immunodominant epitope in native sequence human thrombopoietin is a c-terminal peptide including amino acids 318 to 332:

LNTSYTHSQNLSQEG (SEQ ID NO.: 1)

A modified thrombopoietin is prepared by modifying the amino acids included in that epitope. The amino acids can be modified by deletion, substitution, insertion and/or chemical modification. Modified human thrombopoietin includes a human thrombopoietin with amino acids 1–317 as well as a human thrombopoietin with amino acids 1–311.

A modified human thrombopoietin is preferably prepared by modifying a nucleic acid sequence encoding a native sequence human thrombopoetin. A nucleic acid sequence encoding a native sequence human thrombopoietin can be obtained as described in WO98/52598 and as described in Example 5 below.

Once isolated, the DNA encoding a native sequence of human thrombopoietin is modified using standard techniques such as site-specific mutagenesis to encode a modified polypeptide as described herein. A modified polypeptide produced by recombinant methods is isolated as described above. Alternatively, the native sequence polypeptide can be modified by methods for modifications of polypeptides as described previously.

The modified human thrombopoietin is then analyzed for binding to antibodies to human thrombopoietin from a naive or treated human subject or population thereof and/or from a human or animal dosed with thrombopoietin as determined in the ELISA assays in Example 2. Modified human thrombopoietin that has reduced binding to the antibodies are selected.

A modified thrombopoietin has substantial activity as measured in the HU3 megakaryocytic proliferation assay as described in Example 2. Other assays for determining bioactivity of a modified human thrombopoietin are described in WO98/52598.

III. Administration of the Modified Polypeptide.

The modified polypeptides are designed to have a reduced immunogenicity while retaining substantial therapeutic effects upon administration to a patient. Once at least one immunodominant epitope has been identified and modified as described herein, the modified polypeptide is used therapeutically to treat conditions in a similar manner to use of the native sequence or unmodified polypeptide, if this information is known. The appropriate dosages and means of administration of the modified polypeptide can be determined from information known about the native sequence or unmodified polypeptide.

The modified polypeptides of the present invention are formulated according to known methods to prepare pharmaceutically useful compositions, whereby the modified product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42–96.

When in vivo administration of a modified polypeptide or agonist or antagonist thereof is employed, normal dosage amounts may vary from about 10 ng/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a modified polypeptide is desired in a formulation with release characteristics suitable for the treatment of any disease or disorder requiring administration of the modified polypeptide, microencapsulation of the modified polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.*, 2:795–799 (1996); Yasuda, *Biomed. Ther.*, 27:1221–1223 (1993); Hora et al., *Bio/Technology*, 8:755–758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439–462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1–4.

A modified thrombopoietin can be administered to patients with thrombocytopenia using the dosages and means of administration for native sequence human recombinant thrombopoietin for guidance as is known to those of skill in the art and as described in WO 97/26907 and WO 98/52598.

It will be understood that although a single administration of a thrombopoietin to a patient has been found to be therapeutically effective for the treatment of thrombocytopenia, it can be appreciated that a low-multiple (daily) regimen may be employed, but without appreciable or significant therapeutic significance apart from the obvious clinical disadvantages. It has been found herein that a single dose stimulates the onset of therapeutic response, and although multiple dosing is contemplated herein, perhaps dictated by clinical conditions and practice, termination of dosing after a single or low-multiple administration is independent of therapeutic response.

It has been found that the single or low multiple administration regimen of the present invention is effective at relatively low dosage rates of the order of about 0.1 to 10, preferably about 0.3 to 10, more preferably about 0.5 to 10, still more preferably about 0.5 to 5 $\mu$g/kg body weight of the patient. In single dosing, preferred would be the total administration of about 2±1.5 $\mu$g/kg of body weight. In low-multiple dosing, preferred would be the administration of from about 0.5 to 1.5 $\mu$g/kg of body weight per dose. The above dosages are predicated on preferred intravenous administration. In administration via the subcutaneous route, the total amount administered would be in the range of about one to three times the amount administered via the intravenous route, preferably about two times.

The optimal dosage rate and regimen will be determined by the attending physician taking into consideration various factors known to modify the action of drugs including severity and type of disease, body weight, sex, diet, time and route of administration, other medications and other relevant clinical factors. The regimen will consist of a single or low-multiple administration of a thrombopoietin material hereof in the broad range of from about 0.1 to 100 $\mu$g/kg body weight, preferably a dosage within the range of from about 0.1 to 50 $\mu$g/kg of body weight. A single or low-multiple administration of a dosage ranging from about 0.1 to about 1.0 or more preferably about 0.5 to about 5 $\mu$g/kg produces a therapeutic effect that is therapeutically equivalent to the administration of the same amount of material or more over a regimen spanning daily administration over a number of days upwards of a week or more.

The biologically active modified thrombopoietin materials of the present invention can be administered, in accord herewith, in various routes including via the nose or lung, subcutaneously, and preferably intravenously. In all events, depending upon the route of administration, the biologically active thrombopoietin materials of the present invention are preferably administered in combination with an appropriate pharmaceutically acceptable carrier or excipient. When administered systemically, the therapeutic composition should be pyrogen-free and in a parenterally acceptable solution having due regard for physiological pH isotonicity and stability. These conditions are generally well known and accepted to those of skill in the appropriate art.

The following examples are intended to illustrate but not limit the invention. While they are typical of those that might be used, other procedures are known to those of skill in the art and may alternatively be used.

EXAMPLE 1

Administration of recombinant human TPO causes a dose dependent increase in platelet counts in humans and several animal species, including chimps, rhesus monkeys, baboons, synomolous monkeys and mice. However, we have shown that recombinant TPO is an immunogenic molecule and that antibodies to recombinant TPO can cause problems.

Figure 2:
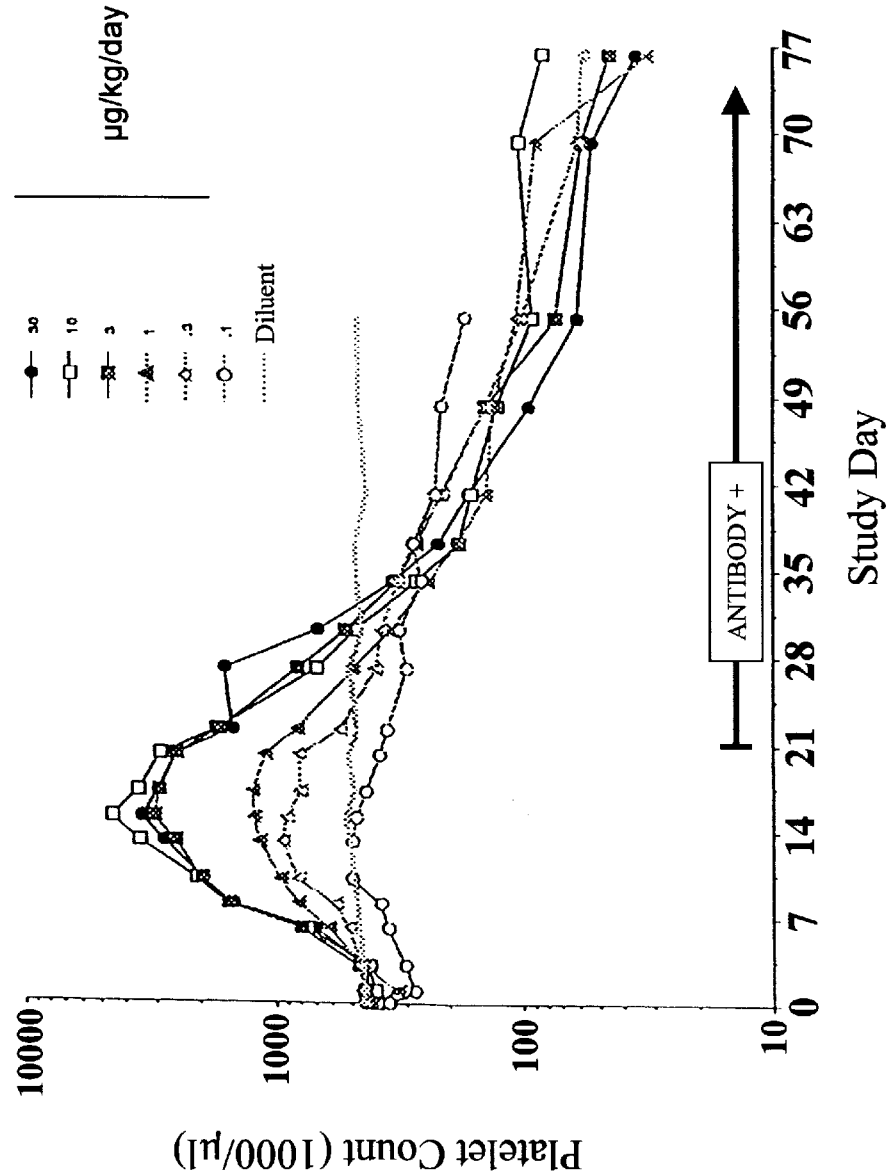

Rhesus monkeys were injected subcutaneously with various doses of recombinant human TPO ranging from 0.1 to 30 $\mu$g/kg for 14 days. Platelet counts and antibodies to TPO were measured over time. FIG. 2 shows platelet profiles in rhesus monkeys injected with various doses of recombinant human TPO. The results show a dose dependent increase in platelet counts reaching a peak between days 14 and 21. However, by day 28 platelets are close to baseline. This downward trend in platelet counts continued throughout entire period of 77 days. All animals were positive for anti-TPO antibodies from day 21 on. These results show that antibodies to TPO can cause thrombocytopenia.

Since there is approximately 15% difference between human and rhesus TPO sequence, we tested the effects of administration of rhesus recombinant TPO in rhesus monkeys on platelet counts and antibody development. Results were very similar: we observed an increase in platelet counts followed by thrombocytopenia, which coincided with occurrence of antibodies (data not shown). We have seen the same phenomenon in mice injected with murine TPO (data not shown). These results indicate that a recombinant polypeptide identical to an endogenous counterpart in a particular species can elicit an antibody response in that species and that the antibody response is detrimental to the animal.

Figure 3:
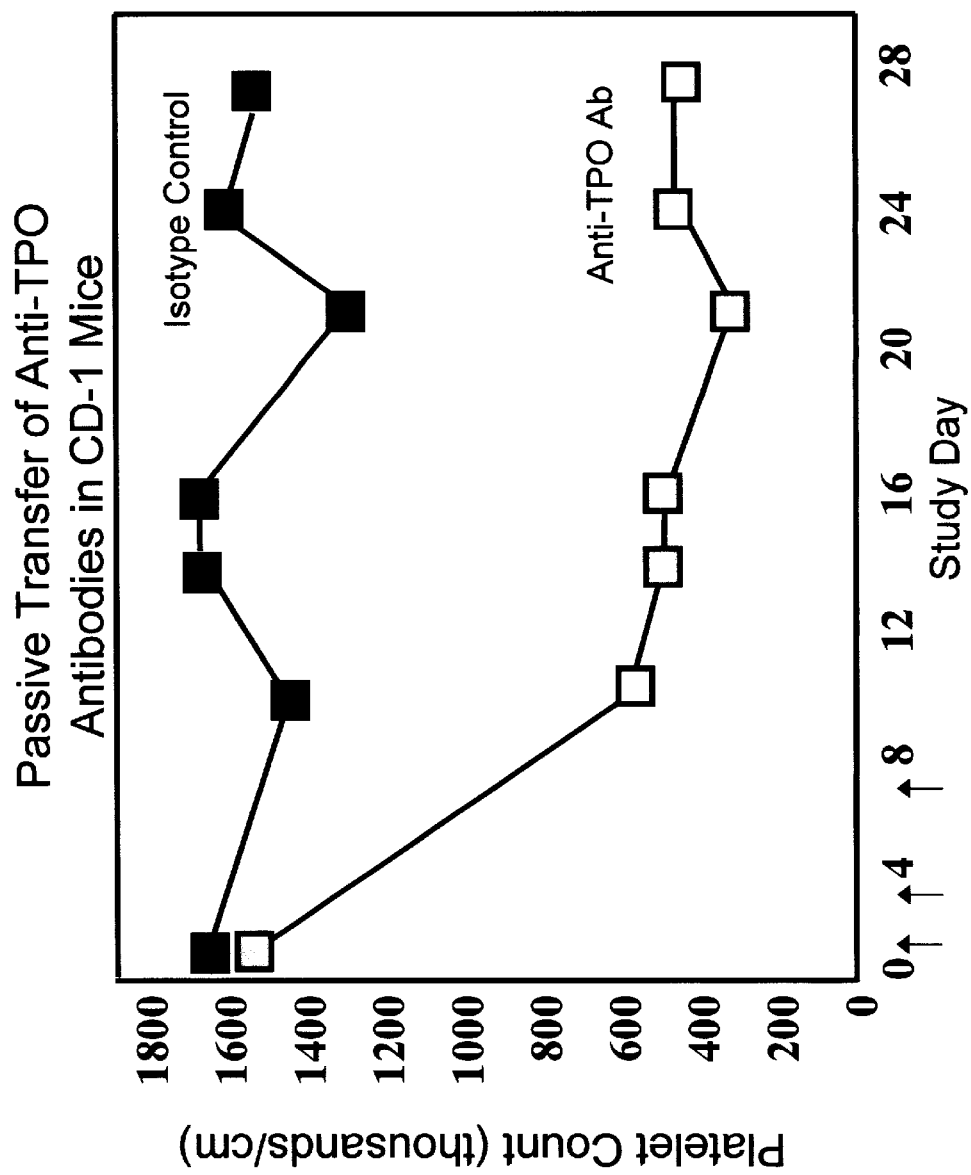
Figure 4A:
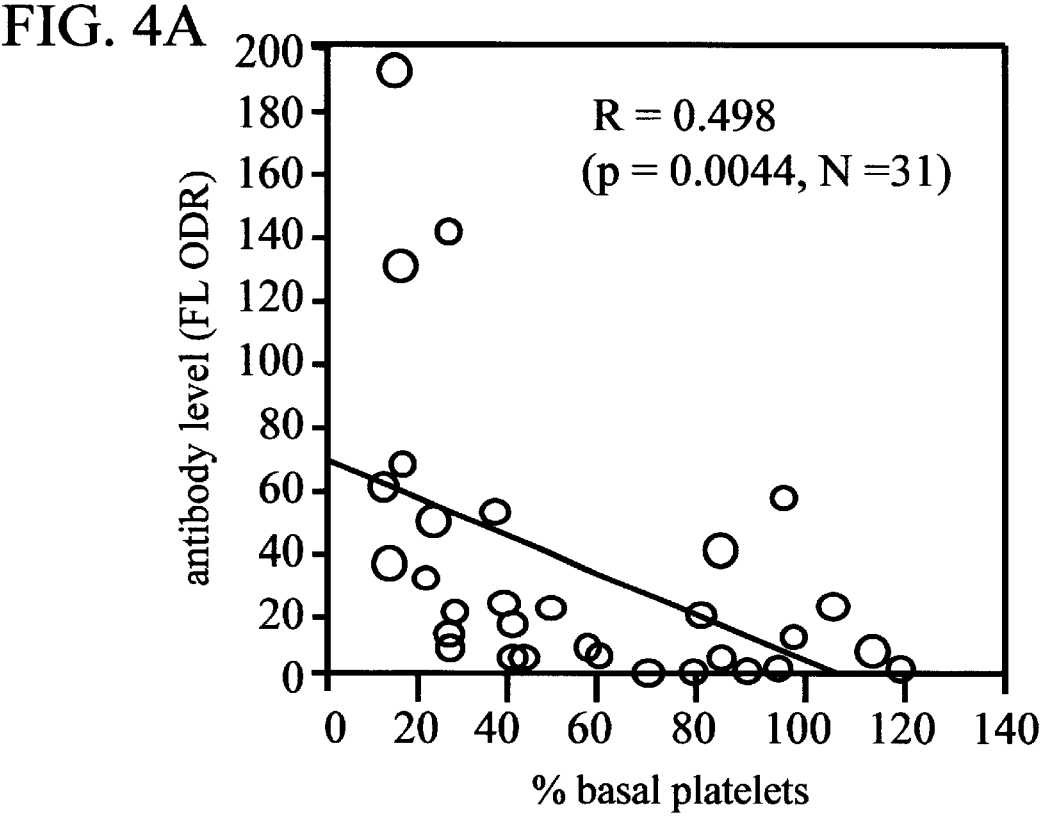
Figure 4B:
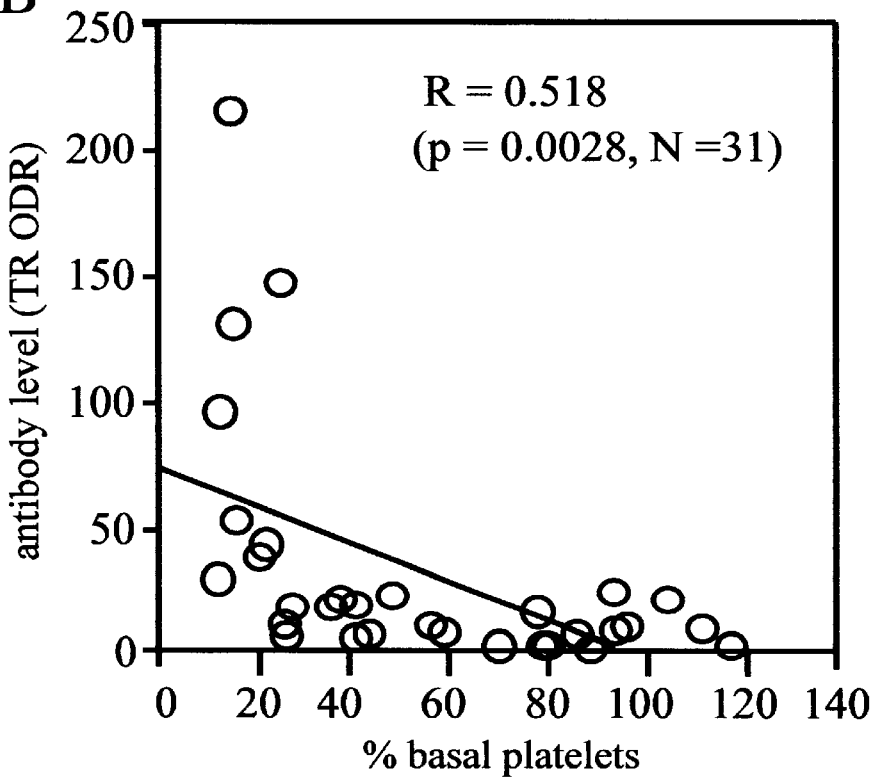
Figure 4C:
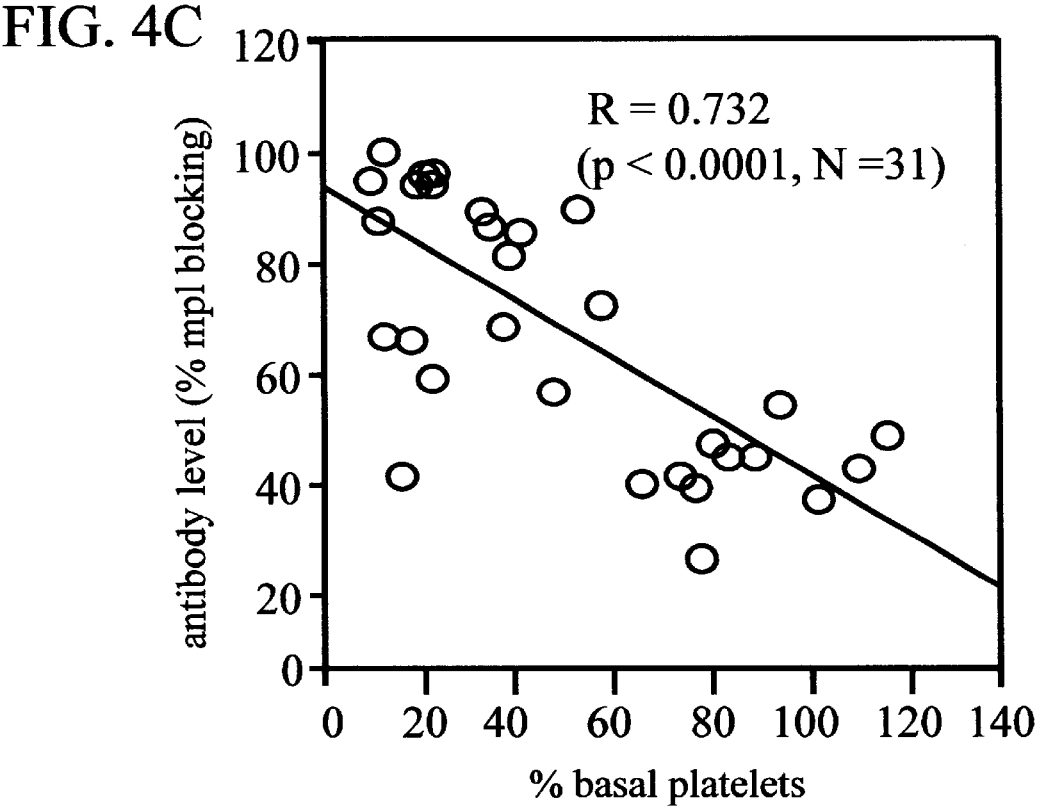
Figure 4D:
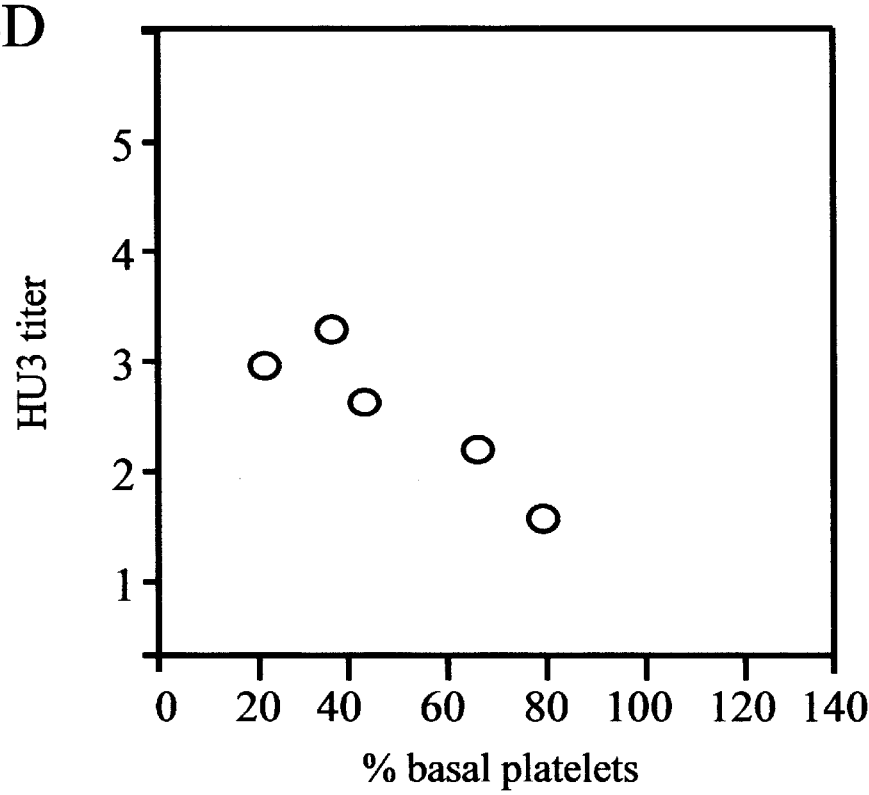
Figure 5:
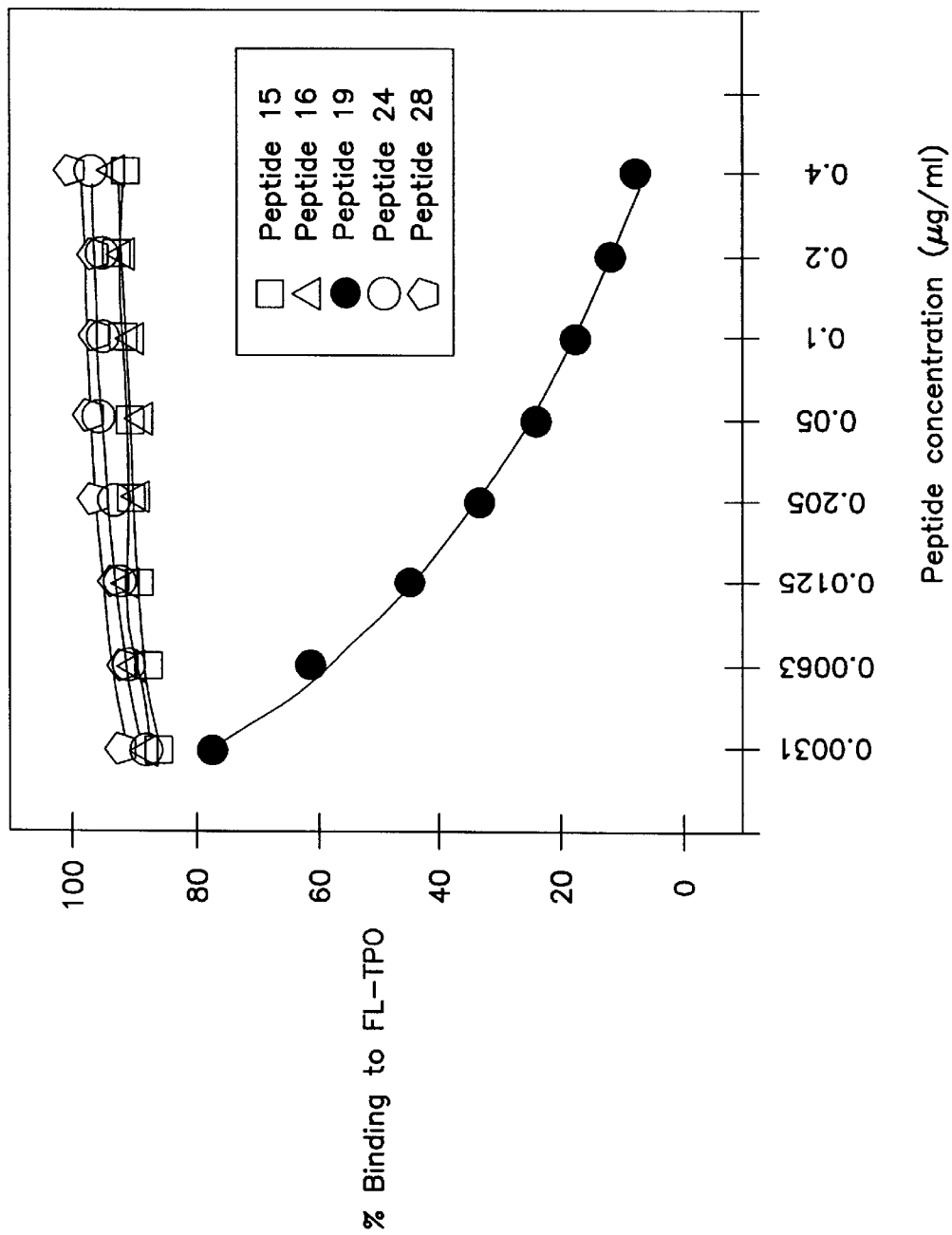

Antibodies to TPO not only coincide with but also can cause thrombocytopenia. An IgG fraction was purified from thrombocytopenic, anti-murine TPO positive mice and injected into naive animals. IgG from normal animals served as a control. The results are shown in FIG. 3. Platelet counts in animals treated with anti-TPO antibodies (shown in open squares) decreased significantly whereas animals injected with control IgG maintained their platelet counts at the baseline level. The results show that antibodies raised against recombinant TPO can neutralize endogenous TPO and cause a drop in platelet counts.

These results show that an antibody response to a therapeutic recombinant polypeptide with an endogenous counterpart is formed in animals dosed with the recombinant polypeptide. The antibody response to the recombinant polypeptide thrombopoietin not only can reduce therapeutic effectiveness of the recombinant polypeptide but can also cause an antibody-mediated thrombocytopenia.

EXAMPLE 2

In addition to the antibody mediated thrombocytopenia described in Example 1, we noticed that approximately 10% of naive animals of all species we examined have preformed antibodies to TPO and normal platelet counts. The species examined include human, rhesus monkeys, chimps and mice. It was surprising that animals had antibodies to an endogenous protein. We characterized the antibody response to human thrombopoietin in human patients.

In order to determine whether the antibodies from human patients were specific for thrombopoietin and also were capable of inhibiting the function of thrombopoietin we developed four different assays.

The following assays were developed to monitor patients' antibody response to TPO: 1) ELISA for antibodies to full length TPO; 2) ELISA for antibodies to truncated TPO, (n-terminal region; amino acids 1–153); 3) ELISA for antibodies that block binding of TPO to recombinant c-mpl receptor ; and 4) a bioassay for antibodies that inhibit proliferation of human megakaryocytic HU3 cells.

Antibodies to full length TPO were also screened in the assays for antibodies for binding to truncated TPO as well as in the receptor blocking and HU3 proliferation assay. Antibodies specific for truncated TPO are also more likely to be antibodies which block or reduce the receptor binding as proliferation of HU3 cells because it is known that the biological activities of TPO are found in the N-terminal region of TPO (amino acids 1–153). Antibodies to full length TPO but not reactive in the assay for binding to truncated TPO, the receptor binding assay, or the HU3 proliferative assay are more likely to be antibodies specific for an epitope in the c-terminal region of TPO.

In ELISA assays for full length and truncated TPO, we used streptavidin coated plates and biotynilated TPO because direct coating of plates with TPO tends to mask the receptor-binding epitope. Human recombinant TPO and truncated TPO are available from Genentech, Inc and can be tagged with biotin using standard methods. Streptavidin-biotin TPO coat, however, created its own problem because of antibodies to streptavidin that are present in some individuals. To avoid this we used the Optical Density Ratio or ODR format in which the same sample is incubated with streptavidin TPO and streptavidin only well. After detection of bound antibodies with anti human IgG-HRP conjugate, the ODR is calculated by dividing the OD in TPO well by the OD of the non-TPO well. The cut off for positivity was determined by repeated analyses of a panel of samples from 50 TPO naive individuals. Mean plus 3 SD principle was used and the cut off ODRs turned out to be 1.5 for the full length and 1.8 for the truncated TPO ELISA.

In the c-mpl blocking ELISA, serum samples were pre-incubated with TPO conjugated with HRP. Methods for making the recombinant C-mpl receptor have been cited in WO 98/52598. TPO is conjugated with HRP using standard methods. The samples were then incubated with receptor-coated wells and OD signal determined. Wells with TPO alone serve as reference. Antibodies that bind to the receptor binding epitope of TPO cause a decrease in signal, which is expressed as a percentage of signal observed in the reference well. Again, using a panel of 50 TPO naive individuals and the same mean plus 3 SD we came up with a cutoff point of 25%. A serum sample that causes 25% or higher decrease in OD is considered positive for antibodies that block binding of TPO to its receptor.

The HU3 bioassay uses human megakaryocytic cell line HU3. Serum samples were heat inactivated, preincubated with TPO, and then incubated with TPO starved cells. HU3 cells are available from Hahnemann University of Philadelphia, Pa. and are described in U.S. Pat. No. 5,128,259. Cell proliferation is determined by measuring alamar-Blue™ reduction. A method for using alamarBlue™ is available from Biosource International, Camarillo, Calif. and described in Ahmed et al, Journal of Immunological Methods 170:211 (1994). Briefly, neutralizing TPO antibodies inhibit cell proliferation which results in a lower alamar-Blue™ signal in comparison with the reference well containing only TPO. alamarBlue™ signals, when measured spectrophotometrically, are measured at 570 and 600 nm. The reduction of alamarBlue™ is expressed as a percentage of decrease in signal caused by antibodies compared to the signal in reference well. The cut off in this assay is 30%, meaning that a serum that causes 30% or higher decrease in signal is considered positive for neutralizing antibodies.

To validate these assays, we studied rhesus monkeys dosed with rhesus recombinant TPO. Antibody levels in all four assays were compared with the degree of thrombocytopenia. Antibody levels, as measured by all 4 assays, were inversely related to platelet counts (FIG. 4). The higher the antibody levels, the lower the platelet counts. It should be pointed out that this inverse relationship is stronger in both functional assays which is expected from assays that are more specific for neutralizing antibodies.

A contingent approach was used to screen clinical samples for anti-TPO immunoreactivity and identify clinically relevant antibody responses using functional assays. The method of screening involves screening serum from patients (naive) before and after (dosed) administration of human recombinant TPO through each of the 4 assays described previously. Samples from all patients were screened pre and post administration of TPO using the FL-TPO ELISA. Positive samples were further analyzed by truncated TPO ELISA and c-mpl blocking ELISA. Samples positive only in FL-TPO assay were considered negative for neutralizing antibodies. Samples positive in FL and TR ELISAs but negative in c-mpl blocking ELISA were also considered negative for neutralizing antibodies. Those that are positive in all three ELISAs were analyzed in HU3 bioassay to confirm the existence of neutralizing antibodies.

In agreement with FDA, we consider human patients positive for neutralizing antibodies if the HU3 assay is positive and associated with clinically significant thrombocytopenia. Results of antibody analysis of serum samples from patients in clinical trials for treatment with recombinant TPO are shown in Table 1.

TABLE 1

Anti-TPO antibodies in patients

|  |  | % positive patients |
| --- | --- | --- |
| Number of patients tested | 379 |  |
| Number of positive patients in: |  |  |
| FL-TPO ELISA | 25 (8*) | (7%) |
| TR-TPO ELISA | 3 (1*) | (<1%) |
| c-mpl blocking ELISA | 2 | (<1%) |
| HU3 proliferation bioassay | 1 | (<1%) |

*number of patients positive for antibodies prior to administration of TPO

Of 379 patients tested, 25 (7%) were positive in FL-TPO ELISA, 17 had induced and 8 had preformed antibodies. Three of the 25 patients positive in FL-TPO assay were also positive in TR-TPO ELISA with one patient with preformed antibody. Two out of the above three patients were also positive in the c-mpl blocking ELISA. Interestingly, only one of the two c-mpl positive sera was positive in the HU3 bioassay. None of the patients, including the one with the positive HU3 result, had clear antibody related thrombocytopenia. It should be pointed out that all of the patients were also receiving chemotherapy.

These results show that some patients had preformed antibodies to TPO before administration of recombinant TPO, and that an antibody response to administration of TPO could be seen in some patients despite the fact that they were immunosuppressed.

EXAMPLE 3

In order to identify the epitopes of recombinant TPO recognized by antibodies from naive and dosed patients, we used a library of rabbit antibodies raised against synthetic TPO peptides of known sequence. Since 90% of all positive patients were positive only in the FL-TPO ELISA, most of the antibodies induced and preformed were directed against the c-terminal half of the molecule. Table 2 shows the list of peptides generated from the c-terminal portion of the molecule with their sequences and lengths as well as ID numbers of corresponding antibodies.

TABLE 2

Synthetic TPO c-terminal epitope peptides and corresponding rabbit anti-peptide antibodies

| peptide sequence (length) | antibody ID # |
|---|---|
| 154–170(17) | 24 |
| 175–190(16) | 48 |
| 195–211(17) | 28 |
| 218–234(17) | 19 |
| 244–259(16) | 17 |
| 258–268(11) | 49 |
| 268–283(16) | 16 |
| 296–311(16) | 51 |
| 318–332(15) | 15 |

The peptides have the following sequences:

| | | |
|---|---|---|
| 154–170 | RAPPTTAVPSRTSLVLT | (SEQ ID NO: 3) |
| 175–190 | PNRTSGLLETNFTASA | (SEQ ID NO: 4) |
| 195–211 | SGLLKWQQGFRAKIPGL | (SEQ ID NO: 5) |
| 218–234 | SLDQIPGYLNRIHELLN | (SEQ ID NO: 6) |
| 244–259 | SRRTLGAPDISSGTSD | (SEQ ID NO: 7) |
| 258–268 | SDTGSLPPNLQ | (SEQ ID NO: 8) |
| 268–283 | QPGYSPSPTHPPTGQY | (SEQ ID NO: 9) |
| 296–311 | VVQLHIPLLPDPSAPTP | (SEQ ID NO: 10) |
| 318–332 | LNTSYTHSQNLSQEG | (SEQ ID NO: 1) |

These antibodies were produced using standard methods and were selected on the basis of their high affinity and strict specificity as measured by competitive binding assays. The binding of anti-peptide 19 to the full length TPO in the presence of increasing concentrations of peptide #19 is inhibited. Binding to full length TPO is not inhibited by peptide 15 or 28, only peptide 19 inhibited rabbit anti-peptide 19. (FIG. 4) The rest of the anti-peptide antibodies showed similar specificity. Although there are some gaps here, more than 80% of the entire c-terminal half is covered.

To characterize both antibodies from naive and dosed humans, in more detail, a number of competitive binding studies were carried out using the above rabbit anti-TPO antibodies of known specificity. Five patients were selected for characterization based on the volume of available serum. Two of them (HH and CPM) had preformed antibodies prior to TPO administration whereas three (PE, CMC, BFJ) developed antibodies during the treatment. The five patients were positive only by the FL-TPO ELISA.

Figure 6:
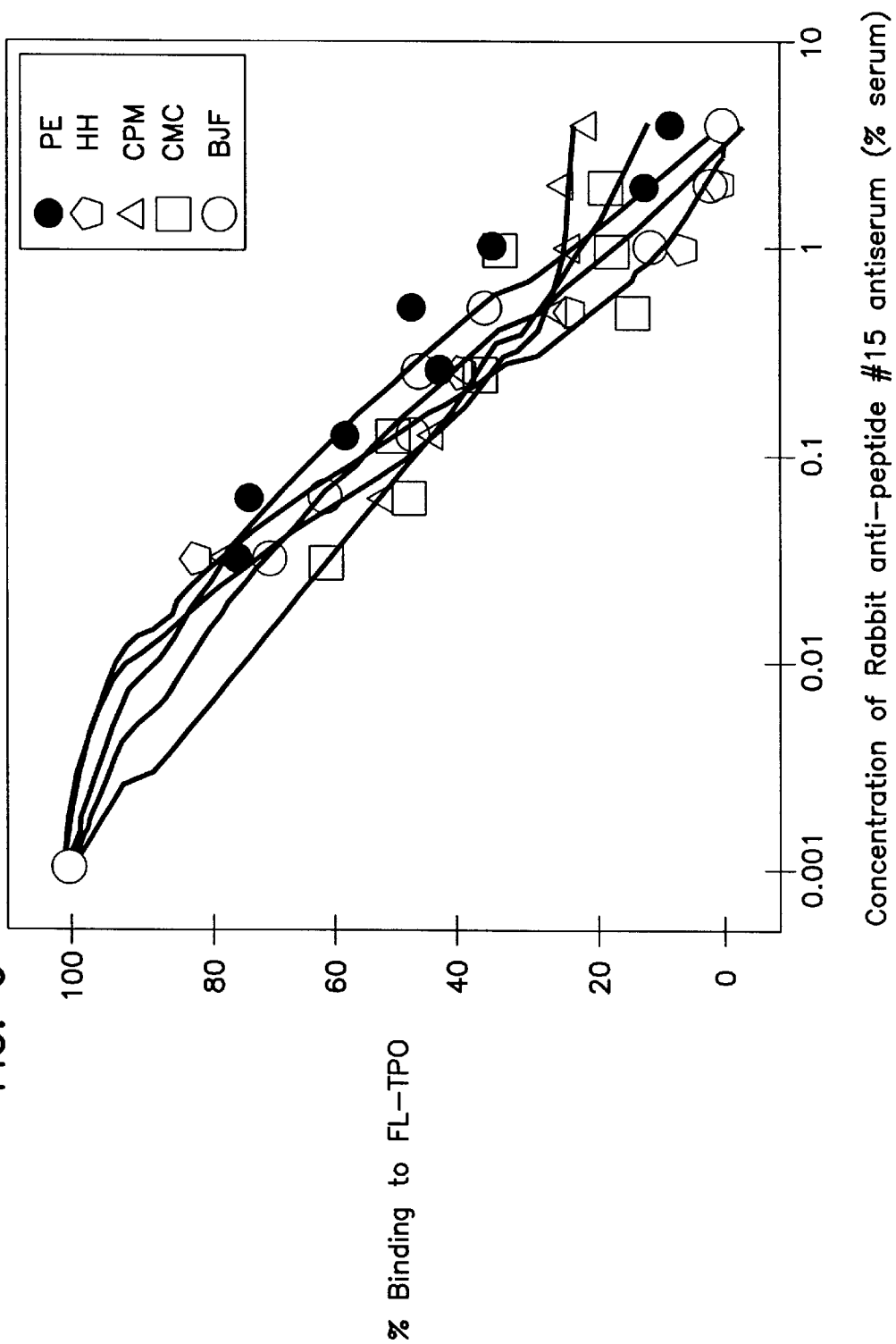

Patients positive exclusively in FL-TPO ELISA had antibodies directed against epitopes comprised within the c-terminal epitope of TPO. Fine specificity of these antibodies was determined by competitive binding against rabbit antibodies specific for 9 different synthetic peptides spanning the c-terminal epitope (Table 2). Only antibodies specific for a peptide including amino acids at the c-terminus (aa318–332) competed with patient's sera (FIG. 6). The competition was complete and equally effective against antibodies from naive patients (HH and CPM) and antibodies from dosed patients(PE, CMC, and BFJ) (FIG. 6). These data indicate that the repertoire of antibodies (naive and induced) directed against the c-terminal epitope of FL-TPO tends to be restricted to an immunodominant epitope at the c-terminal end. These data also indicate that the antibody specificity of antibodies from naive patients is the same as the antibody specificity after dosing or administration of the polypeptide.

EXAMPLE 4

A number of methods of predicting epitopes on the basis of protein sequence are known or have been recently described. Epitopes can be mapped using linear mapping strategy, strategies utilizing computer modeling of 3-D structure of the polypeptide, as well as utilizing software available through such companies as EpiVax, Inc.

The entire linear amino acid sequence of human recombinant TPO was provided to EpiVax, Inc. for analysis and prediction of immunodominant epitopes. The results from EpiVax, Inc. identified 3 regions within the c-terminal epitope that have class II MHC binding motifs. One of these predicted epitope regions (identical to amino acids 312–331) is shown:

TPTSPLLNTSYTHSQNLSQE (SEQ ID NO: 2)

The other 2 epitopes predicted by Epivax were too large to further analyze.

Fourteen out of 15 amino acid residues of the immunodominant peptide identified using antibodies from naive and dosed patients showed 100% homology with the 14 residues at the C-terminal of the 20 amino acid region predicted by EpiVax.

These results indicate that an immunodominant epitope identified on the basis of antibody specificity can be predicted using an analysis of Class II binding motifs in a recombinant polypeptide. The prediction of immunodominant epitopes can be used as a tool to target the region of a molecule to begin epitope mapping of the polypeptide and therefore may save significant time and resources.

Once immunodominant epitopes are predicted or identified using an algorithm, such as provided by Epivax, Inc., the predicted epitopes are also scored for the likelihood of binding to HLA DR and DQ alleles. This information provides an indication of how widespread this immunodominant epitope is recognized in the population. An additional selection criteria may optionally include those immunodominant epitopes that are recognized across a number of HLA types. The epitope or site identified above was found to include a motif that is likely to bind to 11 HLA DR and DQ alleles. These alleles are found in 42.2% Native Americans, 37.3% Caucasians, 26.6% African Americans, and 23.7% Asian Americans.

EXAMPLE 5

The native sequence of TPO is well known. Expression and Purification of Native Sequence Human TPO from CHO as described in WO 98/52598.

1. Description of CHO Expression Vectors

The expression vectors used in the electroporation protocols described below have been designated:

pSV15.ID.LL.MLORF (full length or hTPO332), and

2. Preparation of CHO Expression Vectors cDNA corresponding to the hTPO entire open reading frame was obtained by PCR using the oligonucleotide primes of the following Table.

CHO Expression Vector PCR Primers

Cla.FL.F2 (SEQ ID NO:11)
5' ATC GAT ATC GAT AGC CAG ACA CCC CGG CCA G 3'

ORF.Sal (SEQ ID NO:12)
5' AGT CGA CGT CGA CGT CGG CAG TGT CTG AGA ACC 3'

PRK5hmpl I was used as template for the reaction in the presence of pfu DNA polymerase (Stratagene). Initial denaturation was for 7 min. at 94° C. followed by 25 cycles of amplification (1 min. at 94° C., 1 min. at 55° C. and 1 min. at 72° C.). Final extension was for 15 min. at 72° C. The PCR product was purified and cloned between the restriction sites ClaI and SalI of the plasmid pSV15.ID.LL to obtain the vector pSV15.ID.LL.MLORF. The sequence of the construct was verified.

In essence, the coding sequences for the full length was introduced into the multiple cloning site of the CHO expression vector pSV15.ID.LL. This vector contains the SV40 early promoter/enhancer region, a modified splice unit containing the mouse DHFR cDNA, a multiple cloning site for the introduction of the gene of interest (in this case the TPO sequences described) an SV40 polyadenylation signal and origin of replication and the beta-lactamase gene for plasmid selection and amplification in bacteria.

3. Methodology for Establishing Stable CHO Cell Lines Expressing Recombinant Human $TPO_{332}$ a. Description of CHO Parent Cell Line The host CHO (Chinese Hamster Ovary) cell line used for the expression of the TPO molecules described herein is known as CHO-DP12 (see EP 307,247 published Mar. 15, 1989). This mammalian cell line was clonally selected from a transfection of the parent line (CHO-K1 DUX-B11 (DHFR-)-obtained from Dr. Frank Lee of Stanford University with the permission of Dr. L. Chasin) with a vector expressing preproinsulin to obtain clones with reduced insulin requirements. These cells are also DHFR minus and clones can be selected for the presence of DHFR cDNA vector sequences by growth on medium devoid of nucleoside supplements (glycine, hypoxanthine, and thymidine). This selection system for stably expressing CHO cell lines is commonly used.

b. Transfection Method (Electroporation)

$TPO_{332}$ expressing cell lines were generated by transfecting DP12 cells via electroporation (see e.g. Andreason, G. L. *J. Tiss. Cult. Meth.*, 15, 56 (1993) with linearized pSVI5.ID.LL.MLORF. Three (3) restriction enzyme reaction mixtures were set up for each plasmid cutting; 10 micrograms, 25 micrograms and 50 micrograms of the vector with the enzyme NOTI by standard molecular biology methods. This restriction site is found only once in the vector in the linearization region 3' and outside the TO ligand transcription units. The 100 microliter reactions were set up for overnight incubation at 37 degrees. The next day the mixes were phenol-chloroform-isoamyl alcohol (50:49:1) extracted one time and ethanol precipitated on dry ice for approximately one hour. The precipitate was then collected by a 15 minute microcentrifugation and dried. The linearized DNA was resuspended into 50 microliters of Ham's DMEM-F12 1:1 medium supplemented with standard antibiotics and 2 mM glutamine.

Suspension growing DP12 cells were collected, washed one time in the medium described for resuspending the DNA and finally resuspended in the same medium at a concentration of $10^7$ cells per 750 microliters. Aliquots of cells (750 microliters) and each linearized DNA mix were incubated together at room temperature for one hour and then transferred to a BRL electroporation chamber. Each reaction mix was then electroporated in a standard BRL electroporation apparatus at 350 volts set at 330 micro F and low capacitance. After electroporation, the cells were allowed to sit in the apparatus for 5 minutes and then on ice for an additional 10 minute incubation period. The electroporated cells were transferred to 60 mm cell culture dishes containing 5 ml of standard, complete growth medium for CHO cells (High glucose DMEM-F12 50:50 without glycine supplemented with 1×GHT, 2 mM glutamine, and 5% fetal calf serum) and grown overnight in a 5% $CO_2$ cell culture incubator.

c. Selection and Screening Method

The next day, cells were trypsinized off the plates by standard methods and transferred to 150 mm tissue culture dishes containing DHFR selective medium (Ham's DMEM-F12, 1:1 medium described above supplemented with either 2% or 5% dialyzed fetal calf serum but devoid of glycine, hypoxanthine and thymidine, this is the standard DHFR selection medium we use). Cells from each 60 mm dish were subsequently replated into 5/150 mm dishes. Cells were then incubated for 10 to 15 days (with one medium change) at 37 degrees/15% $CO_2$ until clones began to appear and reached sizes amenable to transfer to 96 well dishes. Over a period of 4–5 days, cell lines were transferred to 96 well dishes using sterile yellow tips on a pipettman set at 50 ml. The cells were allowed to grow to confluency (usually 3–5 days) and then the trays were trypsinized and 2 copies of the original tray were reproduced. Two of these copies were short term stored in the freezer with cells in each well diluted into 50 microliter pf 10% FCS in DMSO. 5 day conditioned serum free medium samples were assayed from confluent wells in the third tray for TPO expression via the Ba/F cell based activity assay. The highest expressing clones based on this assay were revived from storage and scaled up to 2 confluent 150 mm T-flasks for transfer to the cell culture group for suspension adaptation, re-assay and banking.

d. Amplification Protocol

Several of the highest titer cell lines from the selection described above were subsequently put through a standard methotrexate amplification regime to generate higher titer clones. CHO cell clones are expended and plated in 10 cm dishes at 4 concentrations of methotrexate (i.e., 50 nM, 100 nM, 200 nM and 400 nM) at two or three cell numbers ($10^5$, $5 \times 10^5$, and $10^6$ cells per dish). These cultures are then incubated at 37 degree/5% $CO_2$ until clones are established and amendable to transfer to 96 well dishes for further assay. Several high titer clones from this selection were again subjected to greater concentrations of methotrexate (i.e., 600 nM, 800 nM, 1000 nM and 1200 nM) and as before resistant clones are allowed to establish and then transferred to 96 well dishes and assayed.

4. Culturing Stable CHO Cell Lines Expressing Recombinant Human TPO332 and TPO153

Banked cells are thawed and the cell population is expanded by standard cell growth methods in either serum free or serum containing medium. After expansion to sufficient cell density, cells are washed to remove spent cell culture media. Cells are then cultured by any standard method including: batch, fed-batch or continuous culture at 25–40° C., neutral pH, with a dissolved $O_2$ content of at least 5% until the constitutively secreted TPO is accumulated. Cell culture fluid is then separated from the cells by mechanical means such as centrifugation.

5. Purification of Recombinant Human TPO from CHO Culture Fluids

Havested cell culture fluid (HCCF) is directly applied to a BLUE-SEPHAROSE 6 FAST FLOW column (Pharmacia) equilibrated in 0.01 M Na phosphate pH 7.4, 0.15M NaCl at a ratio of approximately 100 L of HCCF per liter of resin and at a linear flow rate of approximately 300 ml/hr/cm². The column is then washed with 3 to 5 column volumes of equilibration buffer followed by 3 to 5 column volumes of 0.01 M Na phosphate pH 7.4, 2.0 M urea. The TPO is then eluted with 3 to 5 column volumes of 0.01 M Na phosphate pH 7.4, 2.0M urea, 1.0M NaCl. The BLUE-SEPHAROSE pool containing TPO is then applied to a wheat germ lectin SEPHAROSE 6 MB column (Pharmacia) equilibrated in 0.01 M Na phosphate pH 7.4, 2.0M urea, and 1.0 M NaCl at a ratio of from 8 to 16 ml of BLUE-SEPHAROSE pool per ml of resin at flow rate of approximately 50 ml/hr/cm². The column is then washed with 2 to 3 column volumes of equilibration buffer. The TPO is then eluted with 2 to 5 column volumes of 0.01 M Na phosphate pH 7.4, 2.0M urea, 0.5 M N-acetyl-D-glucosamine.

The wheat germ lectin pool is then adjusted to a final concentration of 0.04% $C_{12}E_8$ and 0.1% trifluroacid (TFA). The resulting pool is applied to a C4 reverse phase column (Vydac 214TP1022) equilibrated in 0.1% TFA, 0.04% $C_{12}E_8$ at a load of approximately 0.2 to 0.5 mg protein per ml of resin at a flow rate of 157 ml/hr/cm².

The protein is eluted in a two phase linear gradient of acetonitrile containing 0.1% TFA, 0.04% $C_{12}E_8$. The first phase is composed of a linear gradient from 0 to 30% acetonitrile in 15 minutes, the second phase is composed of a linear gradient from 30 to 60% acetonitrile in 60 minutes. The TPO elutes at approximately 50% acetonitrile. A pool is made on the basis of SDS-PAGE.

The C4 pool is then diluted with 2 volumes of 0.01 M Na phosphate pH 7.4, 0.15 M NaCI and diafiltered versus approximately 6 volumes of 0.01 M Na phosphate pH 7.4, 0.15 M NaCI on an AMICOM YM or like ultrafiltration membrane having a 10,000 to 30,000 Dalton molecular weight cut-off. The resulting diafiltrate may be then directly processed or further concentrated by ultrafiltration. The diafiltrate/concentrate is adjusted to a final concentration of 0.01% TWEEN-80.

All or a portion of the diafiltrate/concentrate equivalent to 2 to 5% of the calculated column volume is then applied to a SEPHACRYL S-300 HR column (Pharmacia) equilibrated in 0.01 M Na phosphate pH 7.4, 0.15M NaCI, 0.01% TWEEN-80 and chromatographed at a flow rate of approximately 17 ml/hr/cm². The TPO containing fractions which are free of aggregate and proteolytic degradation products are pooled on the basis of SDS-PAGE. The resulting pool is filtered on a 0.22 micron filter, MILLEX-GV or like, and stored at 2–8° C.

EXAMPLE 6

A nucleic acid encoding a native sequence of human thrombopoietin is isolated as described in Example 5. The nucleic acid encoding a native sequence of human thrombopoietin is modified to encode a modified recombinant human thrombopoietin is modified in one or more amino acids 318–332 or 312–331 (predicted epitope). The method used to modify the nucleic acid sequence to encode the modified human thrombopoietin is site directed mutagenesis.

The modified nucleic acid is transformed into CHO cells for expression of the modified polypeptide as described in Example 5 for native sequence human recombinant thrombopoietin. The modified polypeptide is isolated and purified from CHO cells as described in Example 5.

The modified polypeptide is then tested for binding to an antibody to the polypeptide from a naive human subject or population of human subjects. The modified polypeptide is incubated in an ELISA assay as described in Example 2 with antibodies to the polypeptide from a naive human subject or population thereof and/or with antibodies from a human or animal dosed with the polypeptide. A modified polypeptide that has reduced binding to the antibodies is then analyzed for therapeutic activity of thrombopoietin.

The modified polypeptide is incubated in a c-mpl receptor-binding assay and compared to unmodified or native human thrombopoietin obtained from Genentech, Inc. of San Francisco. The ability of modified thrombopoietin to bind to the receptor can be measured and compared to the binding of unmodified thrombopoietin. In addition, the modified polypeptide can be incubated with the HU3 megakaryocyte cell (available from Hahnemann University of Philadelphia, Pa.) and the ability of the modified polypeptide to stimulate proliferation of the HU3 megakacyocyte cell line is measured using a standard method and compared to the activity of unmodified thrombopoietin. The modified polypeptide preferably has about 60% or more, more preferably about 90% or more of the biological activity of the unmodified thrombopoietin.

The above specification, examples and data provide a complete description of the manufacture and use of the composition of the invention. Since many embodiments of the invention can be made without departing from the spirit and scope of the invention, the invention resides in the claims hereinafter appended. The complete disclosure of all patents, patent documents, and publications herein are incorporated by reference as if individually incorporated.

We claim:

1. A method of modifying a polypeptide, comprising:
   a) identifying at least one immunodominant epitope in a polypeptide that has at least one substantial therapeutic activity, wherein the immunodominant epitope is identified by binding of the epitope to an antibody or population of antibodies obtained from a naive human or animal or population thereof; and
   b) modifying the immunodominant epitope to reduce an immune response to the polypeptide while retaining a substantial therapeutic activity of the polypeptide.

2. A method according to claim 1 wherein the polypeptide has an amino acid sequence that has at least 80% sequence identity to a full-length native sequence or native sequence lacking a signal sequence or an extracellular domain of an endogenous polypeptide in the human or animal.

3. A method according to claim 2, wherein the polypeptide has an amino acid sequence that has about 100% sequence identity to a full-length native sequence or native sequence lacking a signal sequence or an extracellular domain of an endogenous polypeptide in the human or animal.

4. The method according to claim 1, wherein the polypeptide is selected from the group consisting of human thrombopoietin, growth hormones, cytokines, receptors, and humanized antibodies.

5. A method according to claim 1, wherein the animal is selected from the group consisting of primates, cattle, pigs, poultry, and mice.

6. A method according to claim 1, wherein the modification is a deletion of at least one immunodominant epitope.

7. A method according to claim 1, wherein the modification is a modification of at least one amino acid in the immunodominant epitope by N-glycosylation or pegylation.

8. A method according to claim 1, wherein the modification is a mutation of one or more amino acids in at least one immunodominant epitope.

9. A method according to claim 1, wherein the polypeptide is produced in a non human source.

10. A method of modifying a therapeutic polypeptide, comprising:
    a) identifying at least one immunodominant epitope in a therapeutic polypeptide, wherein the immunodominant epitope is identified by binding of the epitope to an antibody or population of antibodies from a naive human or animal or population thereof,
    b) selecting immunodominant epitope that is not located in a region of the polypeptide providing a therapeutic activity of the polypeptide; and
    c) modifying the selected immunodominant epitope to reduce an immune response to the therapeutic polypeptide while retaining the substantial therapeutic activity of the therapeutic polypeptide.

11. A method of modifying a nucleic acid encoding a modified polypeptide comprising:
    a) identifying at least one immunodominant epitope in a polypeptide that has at least one substantial therapeutic activity, wherein the immunodominant epitope is identified by binding of the epitope to an antibody or population of antibodies obtained from a naive human or animal or population thereof;

b) providing an isolate nucleic acid sequence encoding the polypeptide; and c) modifying the isolated nucleic acid to encode a modified polypeptide wherein the modified polypeptide has at least one change in the immunodominant epitope and wherein the change reduces an immune response to the polypeptide while still retaining a substantial therapeutic activity of the polypeptide.

12. A host cell comprising a modified isolated nucleic acid obtained by a method comprising:

a) identifying at least one immunodominant epitope in a polypeptide having at least one substantial therapeutic activity, wherein the immunodominant epitope is identified by binding of the epitope to an antibody or population of antibodies obtained from a naive human or animal or population thereof;

b) providing an isolated nucleic acid sequence encoding the polypeptide; and c) modifying the isolated nucleic acid sequence to encode a modified polypeptide wherein the modified polypeptide has at least one change in the immunodominant epitope and wherein the change reduces an immune response to the polypeptide while still retaining a substantial therapeutic activity of the polypeptide.

13. A method of modifying a polypeptide, comprising:

a) identifying at least one immunodominant epitope in a polypeptide that has at least one substantial therapeutic activity, wherein the immunodominant epitope is identified by binding of the epitope to an antibody or population of antibodies obtained from a naïve union or population thereof; and b) modifying the immunodominant epitope to reduce an immune response to the polypeptide while retaining a substantial therapeutic activity of the polypeptide.

14. A method according to claim 13, wherein the polypeptide is a polypeptide that has an amino acid sequence that has at least 80% amino acid sequence identity to a full length native sequence or native sequence lacking a signal sequence or an extracellular domain of an endogenous polypeptide in the human.

15. A method according to claim 13, wherein the polypeptide is a polypeptide that has an amino acid sequence that has at least 85% amino acid sequence identity to a full length native sequence or native sequence lacking a signal sequence or an extracellular domain of an endogenous polypeptide in the human.

16. A method according to claim 13, wherein the polypeptide is a polypeptide that has an amino acid sequence that has at least 90% amino acid sequence identity to a full length native sequence or native sequence lacking a signal sequence or an extracellular domain of an endogenous polypeptide in the human.

17. A method according to claim 13, wherein the polypeptide is a polypeptide that has an amino acid sequence that has at least 95% amino acid sequence identity to a full length native sequence or native sequence lacking a signal sequence or an extracellular domain of an endogenous polypeptide in the human.

18. A method according to claim 13, wherein the polypeptide is an isolated polypeptide that has amino acid sequence that has about 100% amino acid sequence identity to a full length native sequence or native sequence lacking a signal sequence or an extracellular domain of an endogenous polypeptide in the human.

19. The method according to claim 13, wherein the polypeptide is selected from the group consisting of human thrombopoietin, growth hormones, cytokines, receptors, and humanized antibodies.

20. A method according to claim 13, wherein the modification is a deletion of at least one immunodominant epitope.

21. A method according to claim 13, wherein the modification is a modification of at least one amino acid in the immunodominant epitope by N-glycosylation or pegylation.

22. A method according to claim 13, wherein the modification is a mutation of one or more amino acids in at least one immunodominant epitope.

23. A method according to claim 13, wherein the polypeptide is produced in a non human source.

24. A method of modifying a therapeutic polypeptide, comprising:

a) identifying at least one immunodominant epitope in a therapeutic polypeptide, wherein the immunodominant epitope is identified by binding to an antibody or population of antibodies from a naive human or population thereof, b) selecting the immunodominant epitope that is not located in a region of the polypeptide providing a therapeutic activity of the polypeptide; and c) modifying the selected immunodominant epitope to reduce an immune response to the therapeutic polypeptide while retaining the substantial therapeutic activity of the therapeutic polypeptide.

25. A method of modifying a nucleic acid encoding a modified polypeptide comprising:

a) identifying a least one immunodominant epitope in a polypeptide that has at least one substantial therapeutic activity, wherein the immunodominant epitope is identified by binding to an antibody or population of antibodies obtained from a naive human or population thereof;

b) providing isolated nucleic acid sequence encoding the polypeptide; and c) modifying the isolated nucleic acid to encode a modified polypeptide wherein the modified polypeptide has at least one change in the immunodominant epitope and wherein the change reduces an immune response to the polypeptide while still retaining a substantial therapeutic activity of the polypeptide.

26. A host cell comprising a modified isolated nucleic acid obtained by a method comprising:

a) identifying at least one immunodominant epitope in a polypeptide having at least one substantial therapeutic activity, herein the immunodominant epitope is identified by binding of the epitope to an antibody or population of antibodies obtained from a naive human or population thereof;

b) providing an isolated nucleic acid sequence encoding the polypeptide; and c) modifying the isolated nucleic acid sequence to encode a modified polypeptide wherein the modified polypeptide has at least one change in the immunodominant epitope and wherein the change reduces an immune response to the polypeptide while still retaining a substantial therapeutic activity of the polypeptide.

* * * * *

UNITED STATES PATENT AND TRADEMARK OFFICE
CERTIFICATE OF CORRECTION

PATENT NO. : 6,673,580 B2
DATED : January 6, 2004
INVENTOR(S) : Koren et al.

It is certified that error appears in the above-identified patent and that said Letters Patent is hereby corrected as shown below:

Title page,
Item [56], References Cited, OTHER PUBLICATIONS,"Quijada, L. et al.," reference, "*Immunlogy Letters*" should read -- *Immunology Letters* --
"Chang et al.," reference, "*Pheonotypic*" should read -- *Phenotypic* --
"Cleland," reference, "*Vaccine Design:* The Submit…" should read -- Vaccine Design: The Subunit… --
"Creighton," reference, "*Modecular*" should read -- *Molecular* --
"Hora et al.," reference, "*Released*" should read -- *Release* --
"Hsiao et al.," reference, "Academy of Science" should read -- Academy of Sciences --

Column 12,
Line 18, "followings" should read -- following --

Column 20,
Line 58, "polyomithine" should read -- polyornithine --

Column 23,
Line 28, "Shine-Dalgamo" should read -- Shine-Dalgarno --

Column 24,
Line 12, "untransalated" should read -- untranslated --

Column 32,
Line 51, "cDNA" should read -- A cDNA --

Column 43,
Line 1, "isolate" should read -- isolated --
Line 61, "has amino acid" should read -- has an amino acid --

UNITED STATES PATENT AND TRADEMARK OFFICE
CERTIFICATE OF CORRECTION

PATENT NO.    : 6,673,580 B2
DATED         : January 6, 2004
INVENTOR(S)   : Koren et al.

It is certified that error appears in the above-identified patent and that said Letters Patent is hereby corrected as shown below:

<u>Column 44,</u>
Line 33, "a least" should read -- at least --
Line 52, "herein" should read -- wherein --

Signed and Sealed this

Twenty-second Day of June, 2004

JON W. DUDAS
*Acting Director of the United States Patent and Trademark Office*